(12) United States Patent
Rosén et al.

(10) Patent No.: US 11,096,778 B2
(45) Date of Patent: Aug. 24, 2021

(54) OPHTHALMIC DEVICES, SYSTEM AND METHODS THAT IMPROVE PERIPHERAL VISION

(71) Applicant: AMO Groningen B.V., Groningen (NL)

(72) Inventors: Robert Rosén, Groningen (NL); Theophilus Bogaert, Groningen (NL)

(73) Assignee: AMO Groningen B.V., Groningen (NL)

( * ) Notice: Subject to any disclaimer, the term of this patent is extended or adjusted under 35 U.S.C. 154(b) by 68 days.

(21) Appl. No.: 15/491,843

(22) Filed: Apr. 19, 2017

(65) Prior Publication Data

US 2017/0296330 A1  Oct. 19, 2017

Related U.S. Application Data

(60) Provisional application No. 62/324,783, filed on Apr. 19, 2016.

(51) Int. Cl.
*A61F 2/16* (2006.01)

(52) U.S. Cl.
CPC .......... *A61F 2/1648* (2013.01); *A61F 2/1602* (2013.01); *A61F 2/1613* (2013.01); *A61F 2/1629* (2013.01); *A61F 2002/1681* (2013.01); *A61F 2002/1682* (2015.04); *G02C 2202/10* (2013.01)

(58) Field of Classification Search
CPC .............. A61F 2/1629; A61F 2002/169; A61F 2002/1682; A61F 2/1648; A61F 2/1602; A61F 2/1613
See application file for complete search history.

(56) References Cited

U.S. PATENT DOCUMENTS

| | | | |
|---|---|---|---|
| 3,367,734 A | 2/1968 | Karl et al. |
| 4,581,031 A | 4/1986 | Koziol et al. |
| 4,592,630 A | 6/1986 | Okazaki |
| 4,624,538 A | 11/1986 | MacFarlane |
| 4,637,697 A | 1/1987 | Freeman |
| 4,642,112 A | 2/1987 | Freeman |
| 4,648,878 A | 3/1987 | Kelman |
| 4,655,565 A | 4/1987 | Freeman |
| 4,666,446 A | 5/1987 | Koziol et al. |

(Continued)

FOREIGN PATENT DOCUMENTS

| | | |
|---|---|---|
| EP | 0343067 A1 | 11/1989 |
| EP | 0457553 A2 | 11/1991 |

(Continued)

OTHER PUBLICATIONS

Alfonso J.F., et al., "Prospective Study of the Acri.LISA Bifocal Intraocular Lens," Journal of Cataract Refractive Surgery, Nov. 2007, vol. 33 (11), pp. 1930-1935.

(Continued)

*Primary Examiner* — David H Willse
*Assistant Examiner* — Javier G Blanco
(74) *Attorney, Agent, or Firm* — Johnson & Johnson Surgical Vision, Inc.

(57) ABSTRACT

The present disclosure relates to devices, systems, and methods for improving or optimizing peripheral vision. In particular, various IOL designs, as well as IOL implantation locations, are disclosed which improve or optimize peripheral vision.

11 Claims, 16 Drawing Sheets

(56) References Cited

U.S. PATENT DOCUMENTS

| | | | |
|---|---|---|---|
| 4,778,462 A | 10/1988 | Grendahl | |
| 4,795,462 A | 1/1989 | Grendahl | |
| 4,798,608 A | 1/1989 | Grendahl | |
| 4,798,609 A | 1/1989 | Grendahl | |
| 4,828,558 A | 5/1989 | Kelman | |
| 4,932,970 A | 6/1990 | Portney | |
| 4,995,714 A | 2/1991 | Cohen | |
| 4,995,715 A | 2/1991 | Cohen | |
| 5,016,977 A | 5/1991 | Baude et al. | |
| 5,056,908 A | 10/1991 | Cohen | |
| 5,066,301 A | 11/1991 | Wiley | |
| 5,089,023 A | 2/1992 | Swanson | |
| 5,096,285 A | 3/1992 | Silberman | |
| 5,114,220 A | 5/1992 | Baude et al. | |
| 5,117,306 A | 5/1992 | Cohen | |
| 5,120,120 A | 6/1992 | Cohen | |
| 5,121,979 A | 6/1992 | Cohen | |
| 5,121,980 A | 6/1992 | Cohen | |
| 5,144,483 A | 9/1992 | Cohen | |
| 5,225,858 A | 7/1993 | Portney | |
| 5,229,797 A | 7/1993 | Futhey et al. | |
| 5,354,334 A | 10/1994 | Fedorov et al. | |
| 5,549,669 A | 8/1996 | Jansen | |
| 5,652,638 A | 7/1997 | Roffman et al. | |
| 5,683,457 A | 11/1997 | Gupta et al. | |
| 5,699,142 A | 12/1997 | Lee et al. | |
| 5,715,091 A | 2/1998 | Meyers | |
| 5,728,156 A | 3/1998 | Gupta et al. | |
| 5,748,282 A | 5/1998 | Freeman | |
| 5,760,871 A | 6/1998 | Kosoburd et al. | |
| 5,777,719 A | 7/1998 | Williams et al. | |
| 5,796,462 A | 8/1998 | Roffman et al. | |
| 5,968,094 A | 10/1999 | Werblin et al. | |
| 6,126,283 A | 10/2000 | Wen et al. | |
| 6,126,286 A | 10/2000 | Portney | |
| 6,142,625 A | 11/2000 | Sawano et al. | |
| 6,183,084 B1 | 2/2001 | Chipman et al. | |
| 6,197,057 B1 | 3/2001 | Peyman et al. | |
| 6,210,005 B1 | 4/2001 | Portney | |
| 6,338,559 B1 | 1/2002 | Williams et al. | |
| 6,457,826 B1 | 10/2002 | Lett | |
| 6,464,355 B1 | 10/2002 | Gil | |
| 6,464,725 B2* | 10/2002 | Skotton | A61F 2/1613 623/6.32 |
| 6,474,814 B1 | 11/2002 | Griffin | |
| 6,488,708 B2 | 12/2002 | Sarfarazi | |
| 6,491,721 B2 | 12/2002 | Freeman et al. | |
| 6,527,389 B2 | 3/2003 | Portney | |
| 6,533,416 B1 | 3/2003 | Fermigier et al. | |
| 6,533,814 B1 | 3/2003 | Jansen | |
| 6,536,899 B1 | 3/2003 | Fiala | |
| 6,537,317 B1 | 3/2003 | Steinert et al. | |
| 6,547,822 B1 | 4/2003 | Lang | |
| 6,551,354 B1* | 4/2003 | Ghazizadeh | A61F 2/1629 623/6.34 |
| 6,554,859 B1 | 4/2003 | Lang et al. | |
| 6,557,992 B1 | 5/2003 | Dwyer et al. | |
| 6,609,793 B2 | 8/2003 | Norrby et al. | |
| 6,705,729 B2 | 3/2004 | Piers et al. | |
| 6,808,262 B2 | 10/2004 | Chapoy et al. | |
| 6,830,332 B2 | 12/2004 | Piers et al. | |
| 6,846,326 B2 | 1/2005 | Zadno-Azizi et al. | |
| 6,849,091 B1* | 2/2005 | Cumming | A61F 2/1629 623/6.18 |
| 6,851,803 B2 | 2/2005 | Wooley et al. | |
| 6,913,620 B2 | 7/2005 | Lipshitz | |
| 6,923,539 B2 | 8/2005 | Simpson et al. | |
| 6,923,540 B2 | 8/2005 | Ye et al. | |
| 6,972,033 B2* | 12/2005 | McNicholas | A61F 2/1629 623/6.37 |
| 6,986,578 B2 | 1/2006 | Jones | |
| 7,025,456 B2 | 4/2006 | Morris et al. | |
| 7,025,460 B2 | 4/2006 | Smitth, III | |
| 7,036,931 B2 | 5/2006 | Lindacher et al. | |
| 7,037,338 B2* | 5/2006 | Nagamoto | A61F 2/1613 623/4.1 |
| 7,048,760 B2 | 5/2006 | Cumming | |
| 7,061,693 B2 | 6/2006 | Zalevsky | |
| 7,073,906 B1 | 7/2006 | Portney | |
| 7,137,702 B2 | 11/2006 | Piers et al. | |
| 7,156,516 B2 | 1/2007 | Morris et al. | |
| 7,186,266 B2 | 3/2007 | Peyman | |
| 7,188,949 B2 | 3/2007 | Bandhauer et al. | |
| 7,238,201 B2 | 7/2007 | Portney et al. | |
| 7,287,852 B2 | 10/2007 | Fiala | |
| 7,293,873 B2 | 11/2007 | Dai et al. | |
| 7,365,917 B2 | 4/2008 | Zalevsky | |
| 7,377,640 B2 | 5/2008 | Piers et al. | |
| 7,410,500 B2 | 8/2008 | Claoue | |
| 7,441,894 B2 | 10/2008 | Zhang et al. | |
| 7,475,986 B2 | 1/2009 | Dai et al. | |
| 7,503,655 B2 | 3/2009 | Smith, III | |
| 7,615,073 B2 | 11/2009 | Deacon et al. | |
| 7,665,842 B2 | 2/2010 | Ho et al. | |
| 7,766,482 B2 | 8/2010 | Smith, III et al. | |
| 7,871,162 B2 | 1/2011 | Weeber | |
| 7,997,727 B2 | 8/2011 | Ho et al. | |
| 8,057,034 B2 | 11/2011 | Ho et al. | |
| 8,062,361 B2 | 11/2011 | Nguyen et al. | |
| 8,201,943 B2 | 6/2012 | Hammer et al. | |
| 8,206,442 B2 | 6/2012 | Sel et al. | |
| 8,262,728 B2 | 9/2012 | Zhang et al. | |
| 8,382,832 B2 | 2/2013 | Deacon et al. | |
| 8,430,508 B2 | 4/2013 | Weeber | |
| 8,540,365 B2 | 9/2013 | Varnas | |
| 8,862,447 B2 | 10/2014 | Weeber | |
| 8,894,203 B2 | 11/2014 | Bradley et al. | |
| 9,345,570 B2 | 5/2016 | Sieber et al. | |
| 2002/0044255 A1 | 4/2002 | Ye | |
| 2002/0101564 A1 | 8/2002 | Herrick | |
| 2002/0118337 A1 | 8/2002 | Perrott et al. | |
| 2002/0176049 A1 | 11/2002 | Sakai et al. | |
| 2003/0076478 A1 | 4/2003 | Cox | |
| 2003/0107706 A1 | 6/2003 | Rubinstein et al. | |
| 2003/0171808 A1 | 9/2003 | Phillips | |
| 2003/0214629 A1 | 11/2003 | Luloh et al. | |
| 2004/0085515 A1 | 5/2004 | Roffman et al. | |
| 2004/0106992 A1 | 6/2004 | Lang et al. | |
| 2004/0111153 A1 | 6/2004 | Woods et al. | |
| 2004/0156014 A1 | 8/2004 | Piers et al. | |
| 2004/0237971 A1 | 12/2004 | Radhakrishnan et al. | |
| 2005/0043794 A1 | 2/2005 | Geraghty et al. | |
| 2005/0096226 A1 | 5/2005 | Stock et al. | |
| 2005/0128432 A1 | 6/2005 | Altmann | |
| 2005/0203619 A1 | 9/2005 | Altmann | |
| 2005/0209692 A1* | 9/2005 | Zhang | A61F 2/1629 623/6.34 |
| 2006/0009816 A1 | 1/2006 | Fang et al. | |
| 2006/0030938 A1 | 2/2006 | Altmann | |
| 2006/0058874 A1 | 3/2006 | Peli | |
| 2006/0066808 A1 | 3/2006 | Blum et al. | |
| 2006/0098162 A1 | 5/2006 | Bandhauer et al. | |
| 2006/0109421 A1 | 5/2006 | Ye et al. | |
| 2006/0116763 A1 | 6/2006 | Simpson | |
| 2006/0116764 A1 | 6/2006 | Simpson | |
| 2006/0116765 A1 | 6/2006 | Blake et al. | |
| 2006/0158611 A1 | 7/2006 | Piers et al. | |
| 2006/0227286 A1 | 10/2006 | Hong et al. | |
| 2006/0238702 A1 | 10/2006 | Glick et al. | |
| 2006/0244904 A1 | 11/2006 | Hong et al. | |
| 2006/0247766 A1 | 11/2006 | Marin | |
| 2007/0052920 A1 | 3/2007 | Stewart et al. | |
| 2007/0093891 A1 | 4/2007 | Tabernero et al. | |
| 2007/0129803 A1 | 6/2007 | Cumming et al. | |
| 2007/0171362 A1 | 7/2007 | Simpson et al. | |
| 2007/0182917 A1 | 8/2007 | Zhang et al. | |
| 2007/0182924 A1 | 8/2007 | Hong et al. | |
| 2007/0268453 A1 | 11/2007 | Hong et al. | |
| 2008/0030677 A1 | 2/2008 | Simpson | |
| 2008/0161913 A1 | 7/2008 | Brady et al. | |
| 2008/0161914 A1 | 7/2008 | Brady et al. | |
| 2008/0212024 A1 | 9/2008 | Lai | |
| 2008/0269883 A1 | 10/2008 | Das et al. | |

(56) References Cited

U.S. PATENT DOCUMENTS

| | | |
|---|---|---|
| 2008/0269884 A1 | 10/2008 | Vannoy |
| 2008/0269885 A1 | 10/2008 | Simpson et al. |
| 2008/0269886 A1 | 10/2008 | Simpson et al. |
| 2008/0269890 A1 | 10/2008 | Simpson et al. |
| 2008/0312738 A1 | 12/2008 | Wanders |
| 2009/0018652 A1 | 1/2009 | Hermans et al. |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0198326 A1 | 8/2009 | Zhou et al. |
| 2009/0204211 A1 | 8/2009 | Angelopoulos et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0292354 A1 | 11/2009 | Gontijo et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0100177 A1 | 4/2010 | Zhao |
| 2010/0100178 A1 | 4/2010 | Weeber et al. |
| 2010/0157240 A1 | 6/2010 | Schmid et al. |
| 2010/0161048 A1 | 6/2010 | Schaper, Jr. |
| 2010/0188636 A1 | 7/2010 | Pinto et al. |
| 2010/0204788 A1* | 8/2010 | Van Noy .......... A61F 2/1613 623/6.37 |
| 2011/0130833 A1 | 6/2011 | Scott et al. |
| 2011/0153014 A1 | 6/2011 | Zhang et al. |
| 2011/0279912 A1 | 11/2011 | Fiala |
| 2012/0277857 A1 | 11/2012 | Purchase et al. |
| 2013/0013060 A1 | 1/2013 | Zadno-Azizi et al. |
| 2013/0211515 A1 | 8/2013 | Blum et al. |
| 2013/0226294 A1 | 8/2013 | Van Der Mooren et al. |
| 2014/0022649 A1 | 1/2014 | Eckhardt |
| 2014/0168602 A1 | 6/2014 | Weeber et al. |
| 2014/0253877 A1 | 9/2014 | Li et al. |
| 2015/0005877 A1 | 1/2015 | Wanders |
| 2015/0250583 A1 | 9/2015 | Rosen et al. |
| 2015/0250585 A1 | 9/2015 | Rosen et al. |
| 2015/0265399 A1 | 9/2015 | Rosen et al. |
| 2015/0297342 A1 | 10/2015 | Rosen et al. |
| 2015/0320547 A1 | 11/2015 | Rosen et al. |
| 2016/0067037 A1 | 3/2016 | Rosen et al. |
| 2016/0161364 A1 | 6/2016 | Alarcon Heredia et al. |
| 2016/0193040 A1 | 7/2016 | Qureshi et al. |

FOREIGN PATENT DOCUMENTS

| | | |
|---|---|---|
| EP | 458508 A2 | 11/1991 |
| EP | 681198 A1 | 11/1995 |
| EP | 0926531 A1 | 6/1999 |
| EP | 949529 A2 | 10/1999 |
| EP | 1818023 A1 | 8/2007 |
| EP | 1284687 B1 | 12/2007 |
| EP | 1310267 B1 | 1/2008 |
| EP | 1424049 B1 | 6/2009 |
| WO | 9222264 A1 | 12/1992 |
| WO | 9303409 A1 | 2/1993 |
| WO | 0019906 A1 | 4/2000 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03000154 A2 | 1/2003 |
| WO | 03009053 A1 | 1/2003 |
| WO | 03022137 A2 | 3/2003 |
| WO | 2004034129 A1 | 4/2004 |
| WO | 2004049979 A1 | 6/2004 |
| WO | 2004068214 A1 | 8/2004 |
| WO | 04090611 A2 | 10/2004 |
| WO | 04096014 A2 | 11/2004 |
| WO | 05019906 A1 | 3/2005 |
| WO | 06025726 A1 | 3/2006 |
| WO | 06047698 A1 | 5/2006 |
| WO | 06060477 A2 | 6/2006 |
| WO | 06060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008065362 A1 | 6/2008 |
| WO | 2009076670 A1 | 6/2009 |
| WO | 2009142961 A1 | 11/2009 |
| WO | 2012074742 A1 | 6/2012 |
| WO | 2012083143 A1 | 6/2012 |
| WO | 2013028992 A1 | 2/2013 |
| WO | 2013059041 A1 | 4/2013 |
| WO | 2013105855 A1 | 7/2013 |
| WO | 2013185855 A1 | 12/2013 |
| WO | 2015136375 A2 | 9/2015 |
| WO | 2015136380 A2 | 9/2015 |

OTHER PUBLICATIONS

Atchison D.A., et al., "Shape of the Retinal Surface in Emmetropia and Myopia," Investigative Ophthalmology & Visual Science, Aug. 2005, vol. 46 (8), pp. 2698-2707.

Baskaran K., et al., "Benefit of Adaptive Optics Aberration Correction at Preferred Retinal Locus," Optometry and Vision Science, Sep. 2012, vol. 89 (9), pp. 1417-1423.

Buralli D.A., et al, "Optical Performance of Holographic Kinoforms," Applied Optics, Mar. 1989, vol. 28 (5), pp. 976-983.

Canovas C., et al., "Hybrid Adaptive-Optics Visual Simulator," Optical Letters, Jan. 15, 2010, vol. 35 (2), pp. 196-198.

Cohen A.L., "Practical Design of a Bifocal Hologram Contact Lens or Intraocular Lens," Applied Optics, Jul. 1, 1992, vol. 31 (19), pp. 3750-3754.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, Apr. 1992, vol. 1780, pp. 393-402.

Escudero-Sanz I., et al., "Off-Axis Aberrations of a Wide-Angle Schematic Eye Model," Journal of the Optical Society of America. A, Optics, Image Science, and Vision, Aug. 1999, vol. 16 (8), pp. 1881-1891.

Hoffmann, P.C., et al., "Analysis of Biometry and Prevalence Data for Corneal Astigmatism in 23 239 Eyes," Journal of Cataract and Refractive Surgery, Sep. 2010, vol. 36(9), pp. 1479-1485.

International Search Report and Written Opinion for Application No. PCT/IB2015/000989, dated Sep. 8, 2015, 13 pages.

International Search Report and Written Opinion for Application No. PCT/IB2015/001027, dated Sep. 8, 2015, 14 pages.

International Search Report and Written Opinion for Application No. PCT/IB2015/001244, dated Nov. 8, 2015, 14 pages.

International Search Report and Written Opinion for Application No. PCT/IB2015/001588, dated Oct. 15, 2015, 11 pages.

International Search Report and Written Opinion for Application No. PCT/IB2015/002000, dated Feb. 12, 2016, 12 pages.

International Search Report and Written Opinion for Application No. PCT/US2012/052311, dated Dec. 21, 2012, 14 pages.

International Search Report and Written Opinion for Application No. PCT/US2014/020343, dated May 15, 2014, 10 pages.

Jaeken B., et al., "Comparison of the Optical Image Quality in the Periphery of Phakic and Pseudophakic Eyes," Investigative Ophthalmology & Visual Science, May 1, 2013, vol. 54 (5), pp. 3594-3599.

Jafari-Nodoushan M., et al., "Control-Flow Checking Using Branch Instructions," IEEE/IFIP International Conference on Embedded and Ubiquitous Computing, Dec. 17-20, 2008, pp. 66-72.

Lewis P., et al., "Resolution of Static and Dynamic Stimuli in the Peripheral Visual Field," Vision Research, Aug. 15, 2011, vol. 51 (16), pp. 1829-1834.

Liou H.L., et al., "Anatomically Accurate, Finite Model Eye for Optical Modeling," Journal of Optical Society of America, Aug. 1997, vol. 14 (8), pp. 1684-1695.

(56) References Cited

OTHER PUBLICATIONS

Liou H.L., et al., "The Prediction of Spherical Aberration with Schematic Eyes," Ophthalmic and Physiological Optics, Jan. 1996, vol. 16 (4), pp. 348-354.

Lundstroma L., et al., "Symmetries in Peripheral Ocular Aberrations," Journal of Modern Optics, Mar. 16, 2011, vol. 58 (19-20), pp. 1690-1695.

Marsack J.D., et al., "Metrics of Optical Quality Derived from Wave Aberrations Predict Visual Performance," Journal of Vision, Apr. 2004, vol. 4 (4), pp. 322-328.

Monsoriu J.A., et al., "Devil's Lenses," Optics Express, Oct. 17, 2007, vol. 15 (21), pp. 13858-13864.

Norrby S., et al., "Model Eyes for Evaluation of Intraocular Lenses," Applied Optics, Sep. 7, 2007, vol. 46 (26), pp. 6595-6605.

Oh N., et al., "Control-Flow Checking by Software Signatures," IEEE Transactions on Reliability, Mar. 2, 2002, vol. 51 (2), pp. 111-122.

Piers P.A., et al., "Eye Models for the Prediction of Contrast Vision in Patients with New Intraocular Lens Designs," Optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

Rosen R., et al., "Adaptive Optics for Peripheral Vision," Journal of Modern Optics, Jul. 10, 2012, vol. 59 (12), pp. 1064-1070.

Rosen R., et al., "Evaluating the Peripheral Optical Effect of Multifocal Contact Lenses," Ophthalmic and Physiological Optics, Nov. 2012, vol. 32 (6), pp. 527-534.

Rosen R., et al., "Have We Misinterpreted the Study of Hoogerheide Et Al. (1971)?," Optometry and Vision Science, Aug. 2012, vol. 89 (8), pp. 1235-1237.

Rosen R., et al., "Sign-dependent Sensitivity to Peripheral Defocus for Myopes Due to Aberrations," Investigative Ophthalmology & Visual Science, Oct. 17, 2012, vol. 53 (11), pp. 7176-7182.

Rosen R., et al., "Influence of Optical Defocus on Peripheral Vision," Visual Psychophysics and Physiological Optics, Jan. 2011, vol. 52 (1), pp. 318-323.

Rosen R., "Peripheral Vision: Adaptive Optics and Psychophysics," Doctoral Thesis Department of Applied Physics Royal Institute of Technology Stockholm, Sweden Apr. 2013, 86 pages.

Shammas, J.H., "Intraocular Lens Power Calculations," Chapter 12, "Ultrasound Measurement of the Challenging Eye," Slack Incorporated, p. 117, Copyright 2004.

Siedlecki D., et al., "Radial Gradient index Intraocular Lens: a Theoretical Model," Journal of Modern Optics, Feb. 20-Mar. 10, 2008, vol. 55 (4-5), pp. 639-647.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Villegas E.A., et al., "Correlation between Optical and Psychophy, Sical Parameters as a Function of Defocus," Optometry and Vision Science, Jan. 1, 2002, vol. 79 (1), pp. 60-67.

International Search Report and Written Opinion for Application No. PCT/IB2017/000553, dated Aug. 28, 2017, 19 pages.

International Search Report and Written Opinion for Application No. PCT/IB2017/000318, dated Aug. 4, 2017, 14 pages.

\* cited by examiner

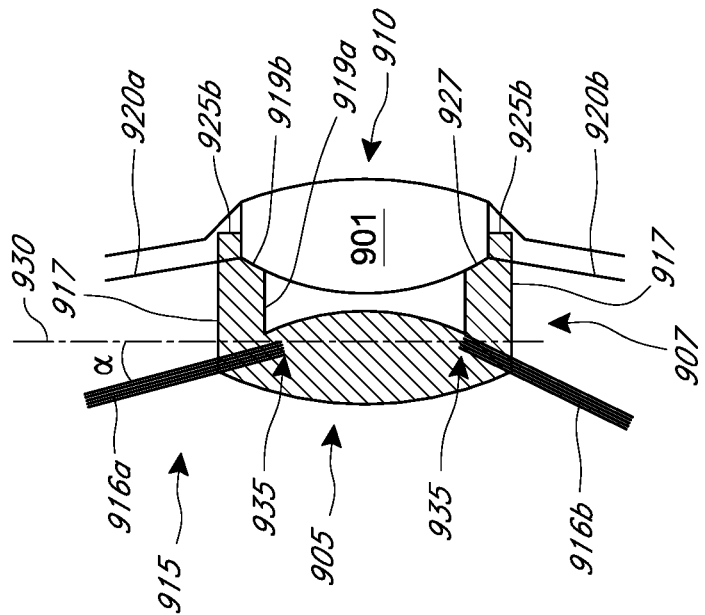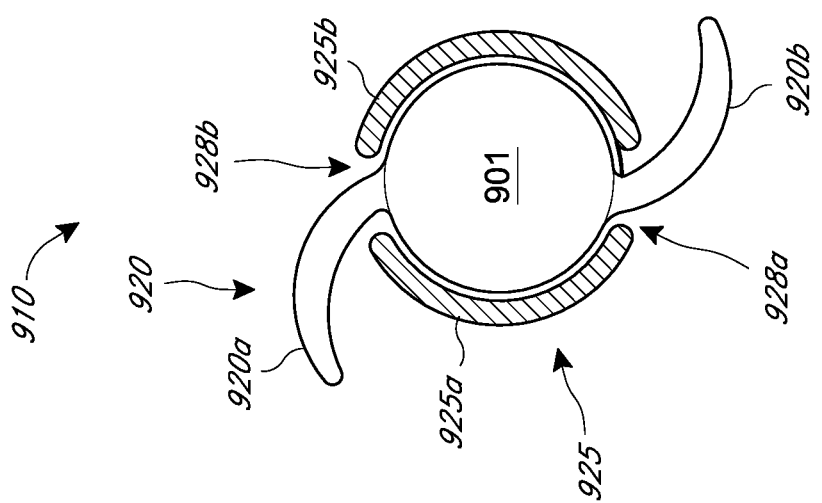
FIG. 9A
FIG. 9B

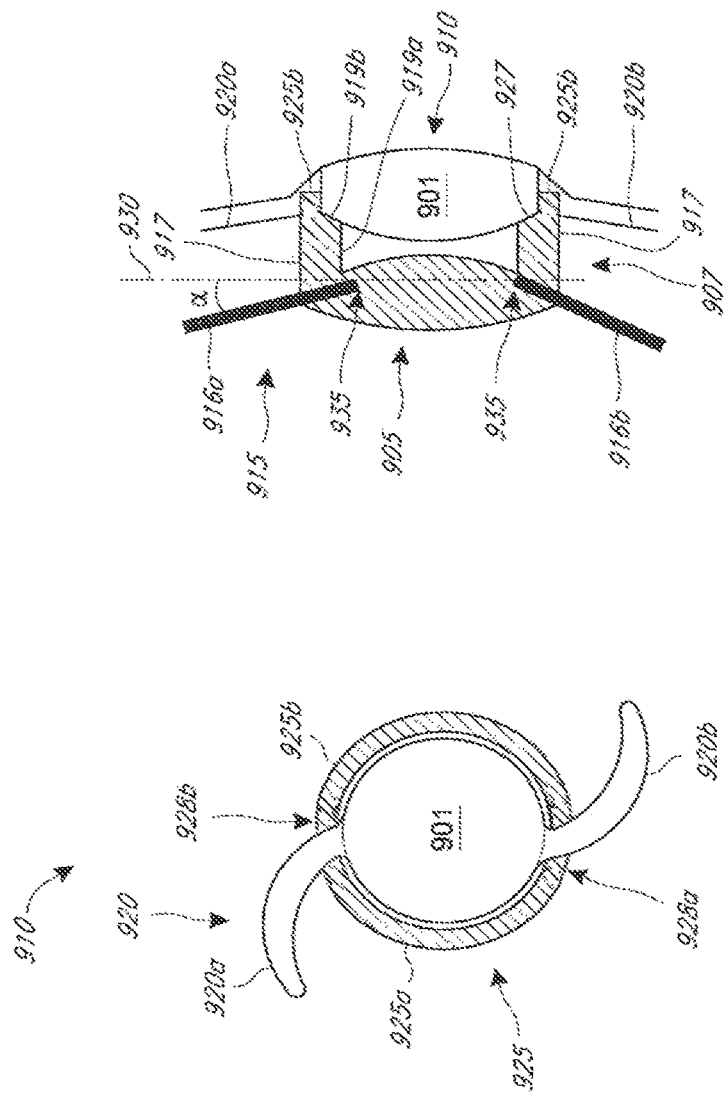

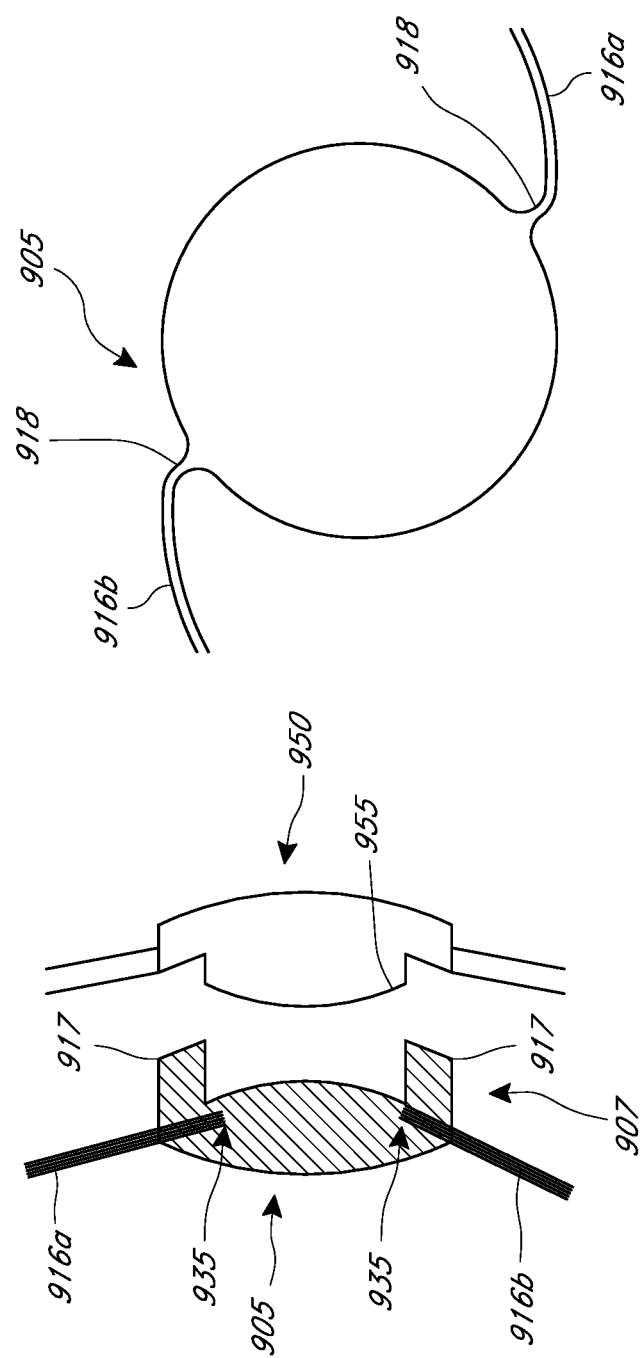

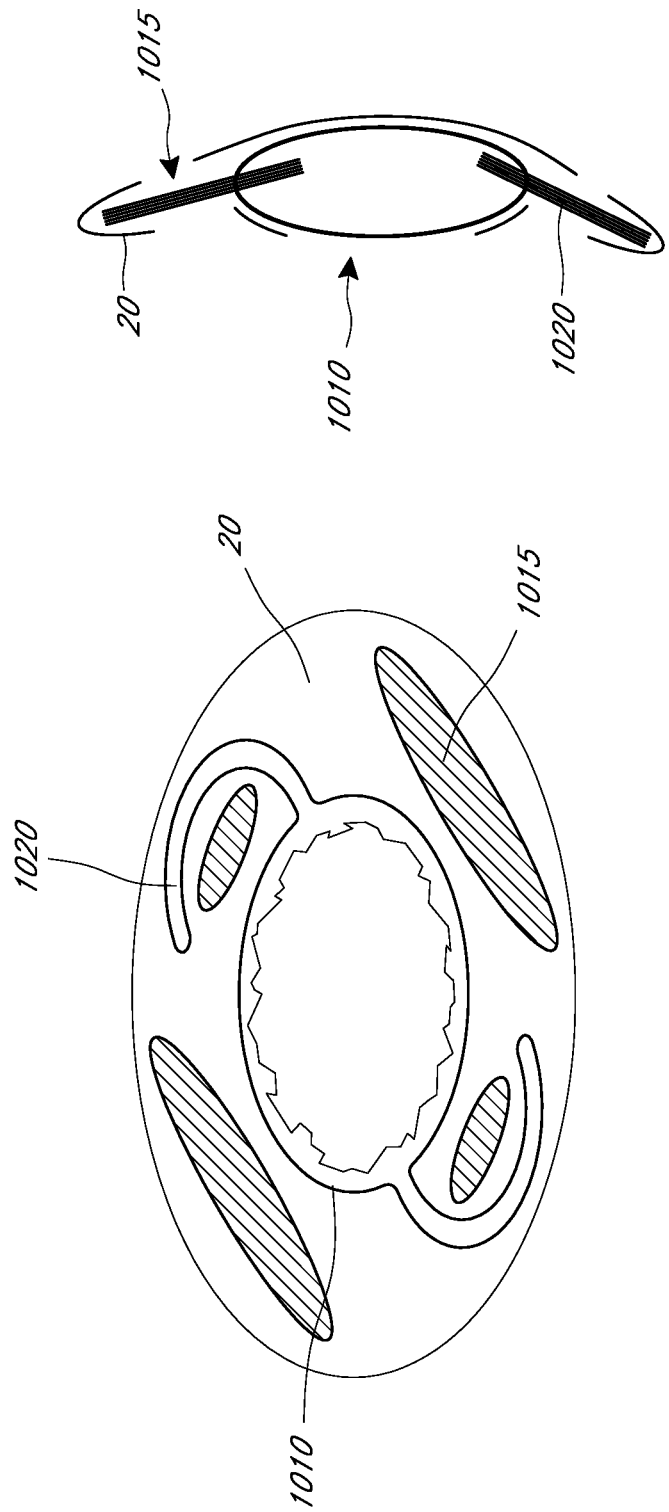

OPHTHALMIC DEVICES, SYSTEM AND METHODS THAT IMPROVE PERIPHERAL VISION

RELATED APPLICATIONS

This application claims priority to, and the benefit of, under 35 U.S.C. § 119(e) of U.S. Provisional Appl. No. 62/324,783, filed Apr. 19, 2016, which is incorporated by reference herein in its entirety.

BACKGROUND

Field

This disclosure generally relates to devices, systems and methods that improve peripheral vision.

Description of Related Art

Intraocular Lenses (IOLs) may be used for restoring visual performance after a cataract or other ophthalmic procedure in which the natural crystalline lens is replaced with or supplemented by implantation of an IOL. When such a procedure changes the optics of the eye, generally a goal is to improve vision in the central field. Recent studies have found that, when a monofocal IOL is implanted, peripheral aberrations are changed, and that these aberrations differ significantly from those of normal, phakic eyes. The predominant change is seen with respect to peripheral astigmatism, which is the main peripheral aberration in the natural eye, followed by sphere, and then higher order aberrations. Such changes may have an impact on overall functional vision, on myopia progression, and—for newborns and children—on eye development.

There are also certain retinal conditions that reduce central vision, such as AMD or a central scotoma. Other diseases may impact central vision, even at a very young age, such as Stargardt disease, Best disease, and inverse retinitis pigmentosa. The visual outcome for patients suffering from these conditions can be improved by improving peripheral vision.

SUMMARY

The systems, methods and devices of the disclosure each have several innovative aspects, no single one of which is solely responsible for the desirable attributes disclosed herein.

Various systems, methods and devices disclosed herein are directed towards intraocular lenses (IOLs) including, for example, posterior chamber IOLs, phakic IOLs and piggyback IOLs, which are configured to improve peripheral vision. For normal patients, e.g., uncomplicated cataract patients, peripheral vision may be balanced with good central vision in order to improve or maximize overall functional vision. For those patients having a pathological loss of central vision, peripheral vision may be improved or maximized, taking into account the visual angle where the retina is healthy.

In various embodiments disclosed herein, the principal plane of an IOL previously implanted/to be implanted in the eye of a patient (also referred to herein as an existing IOL) is moved posteriorly, further from the iris and towards the retina, closer to the nodal point of the eye as compared to standard IOLs that are currently being implanted. This can effectively change the field curvature in the image plane, to better align with the shape of the retina. The location of the principal plane of the existing IOL can be shifted (e.g., posteriorly) by displacing the existing IOL axially from its original axial position to a displaced axial location farther from the iris. The displaced axial location is rearward of the location of the principal plane (or anterior surface of a standard IOL) or the location of the principal plane of a natural lens. Displacing the principal plane of the existing IOL posteriorly relative to the iris can reduce peripheral aberrations of the eye which in turn can improve peripheral vision. Accordingly, the axial position of the existing IOL can be selected to reduce one or more peripheral aberrations to improve peripheral vision relative to a standard IOL while accounting for other visual tradeoffs such as on-axis image quality. In various embodiments disclosed herein, the principal plane (or the anterior surface) of an existing IOL can be moved posteriorly by mechanically pushing the existing lens by an add-on lens (e.g., a piggyback lens). The existing IOL can be pushed rearward toward the retina by a desired distance when the add-on lens is implanted in the eye. After the existing IOL is pushed to its desired axial location, the connections between the add-on lens and the existing IOL in conjunction with the structure and material properties of haptic systems attached to the existing IOL and the add-on lens can be relied upon to maintain the existing IOL at its desired axial location.

In some embodiments, the axial position of the existing IOL is between about 1.5 mm and about 2.5 mm behind the iris. For example, the axial position of the existing IOL may be about 1.9 mm behind the iris. In certain embodiments, the axial position of the existing IOL is between about 2.5 mm and about 3.5 mm behind the iris. For example, the axial position of the existing IOL may be about 2.9 mm behind the iris. In some embodiments, the axial position of the existing IOL may be between about 3.5 mm and about 4.1 mm behind the iris. For example, the axial position of the existing IOL may be about 3.9 mm behind the iris. For dimensions of an average eye, the position of the existing IOL may be limited by the vitreous body, to not exceed about 4.5 mm behind the iris. In such embodiments, portions of the capsular bag and/or vitreous humour may be removed to make space for the existing IOL. For some embodiments of the existing IOLs, the principal plane can be about 0.4 mm posterior to the anterior lens surface. Thus, when the anterior surface of the existing IOL is at a distance, 's' (e.g., 1.5 mm) behind the iris, the principal plane of the existing IOL is at a distance of about 's+0.4 mm' (e.g., 1.9 mm) behind the iris.

In various embodiments, the existing IOL may be a multifocal lens, a lens including a prism, or a telescope lens, having the principal plane moved posteriorly by one of the methods described herein.

In some embodiments, characteristics of the retina are considered when determining the desired displacement for the existing IOL and/or when determining the optical characteristics of the add-on lens (e.g., the piggyback lens). In particular, the desired axial displacement of the existing IOL and/or the optical characteristics of the add-on lens can be determined from a geographical map of retinal functionality and/or the retinal shape combined with other ocular geometry, such as pupil size and location, axial positions of the pupil, lens, and retina, anterior and/or posterior corneal aberrations, tilts and decentrations within the eye. A metric function can be used to improve or optimize the optical characteristics of the add-on lens and/or the desired displacement of the existing IOL, accounting for both central and peripheral optical quality.

In some embodiments, a dual-optics IOL system can be used to improve natural vision by reducing peripheral aberrations. The dual-optics lens can comprise an anterior member and a posterior member. In various embodiments, the anterior member can be a lens (e.g., a piggyback lens) and the posterior lens can be an existing IOL or an IOL implanted to provide corrective refractive benefits. In various embodiments, the anterior member can be configured to push the existing IOL or the implanted IOL posteriorly so as to displace the principal plane of the existing IOL or the implanted IOL posteriorly in order to reduce peripheral aberrations and improve peripheral vision. In various embodiments, the anterior member can be configured to only push the existing IOL or the implanted IOL posteriorly without providing any optical correction.

An innovative aspect of the subject matter disclosed herein is implemented in an ophthalmic lens configured to improve vision for a patient's eye. The lens comprises an optic with a first surface and a second surface opposite the first surface, the first surface and the second surface meeting at a circumference, wherein the optic together with a cornea and an existing lens in the patient's eye is configured to improve image quality of an image produced by light incident on the patient's eye in an angular range between about 1 degree and about 50 degrees with respect to the optical axis and focused at a peripheral retinal location disposed at a distance from the fovea. The lens further comprises a haptic comprising at least a first arm comprising a first end coupled with a first location of the circumference and a second arm comprising a first end coupled with a second location of the circumference, the first arm extending radially and anteriorly away from the first location, the second arms extending radially and anteriorly away from the second location. The lens also comprises a posterior displacer projecting posteriorly from the circumference of the optic to a free end configured to couple with the existing lens. Each of the first and second arm comprises a second end configured to brace against an ocular structure and when so braced to position the posterior displacer in contact with and at a location posterior of the existing lens whereby the existing lens is shifted posteriorly in the eye to displace the principle plane of the existing lens posteriorly in the eye by a distance 'd'.

In various embodiments, the posterior displacer can be configured to contact an arcuate member disposed about an anterior face of the existing lens. The arcuate member can comprise a first ring segment disposed between two ends and a second ring segment disposed between two ends, adjacent ends of the first and second ring segments each forming one or more gap to receive a haptic of the existing lens. The posterior displacer can comprise a notch having a first portion configured to be disposed along a side portion of the existing lens and a second portion configured to be disposed along an anterior surface of the existing lens. The posterior displacer can comprise an anteriorly angled face configured to mate with a posteriorly angled face of the anterior side of the existing lens. The posterior displacer can comprise an anteriorly angled face configured to mate with a posteriorly angled face of the anterior side of the existing lens. The second surface of the optic can be configured to be spaced away from the anterior face of the existing lens at the central optical axis of the existing lens when the posterior displacer is in contact with the existing lens. The second surface of the optic can comprise a soft material configured to be in contact with the anterior face of the existing lens at a central optical axis thereof when the posterior displacer is in contact with the existing lens. The optic can comprise an anterior portion and a posterior portion, the posterior portion comprising the second surface of the optic. The posterior portion can comprise a soft material configured to be in contact with the anterior face of the existing lens at a central optical axis thereof when the posterior displacer is in contact with the existing lens. The displacer can comprise a rigid ring disposed within a soft material, the soft material configured to be in contact with the anterior face of the existing lens at a central optical axis thereof when the posterior displacer is in contact with the existing lens.

An innovative aspect of the subject matter disclosed herein is implemented in a method of improving vision quality in a human eye at locations spaced away from the fovea, the human eye having an artificial intraocular lens disposed therein. The method comprises accessing an anterior chamber of the human eye; advancing a lens shifter into the anterior chamber, the lens shifter comprising an intraocular lens surface contact member and a peripheral ocular tissue contact member; placing a free end of the peripheral ocular tissue contact member in contact with peripheral ocular tissue of the anterior chamber at a first location along an anterior-posterior direction, the tissue contact member disposed in a direction posteriorly and radially inwardly toward the optical axis of the eye to the intraocular lens surface contact member to a second location along an anterior-posterior direction at which the tissue contact member is coupled with the intraocular lens surface contact member; coupling the intraocular lens surface contact member with an anterior surface of the artificial intraocular lens; and releasing the lens shifter in the anterior chamber such that the lens shifter reaches a rest state after displacing the principle plane of the artificial intraocular lens posteriorly by a distance d whereby the peripheral image quality of the eye is improved.

Various embodiments of the method can further comprise modifying a lens capsule of the human eye to reduce the stiffness of the lens capsule, the lens capsule having the artificial intraocular lens disposed therein. Various embodiments of the method can further comprise ablating a region of the anterior lens capsule anterior. In some embodiments, ablating can include removing portions of anterior portions of the anterior capsule nasally and/or temporally of the artificial intraocular lens. In some embodiments, ablating can include removing portions of anterior portions of the anterior capsule nasally and/or temporally of the artificial intraocular lens. Various embodiments of the method can include ablating a region of the lens capsule between an optic and a portion of a haptic thereof. Various embodiments of the method can include ablating a region of the lens capsule that is larger than a capsulorhexis of the human eye. Various embodiments of the method can include ablating a plurality of apertures smaller than a capsulorhexis of the human eye. For example, in some embodiments more than 20 apertures smaller than a capsulorhexis of the human eye can be ablated. In various embodiments, the apertures can be circumferentially elongated. Various embodiments of the method can include modifying a portion of the human eye posterior of a lens capsule of the human eye to create space prior to releasing the lens shifter. Modifying the portion of the human eye posterior of a lens capsule of the human eye can include removing at least a portion of a posterior capsule. Modifying the portion of the human eye posterior of a lens capsule of the human eye can include removing at least a portion of a vitreous capsule.

Another innovative aspect of the subject matter disclosed herein can be implemented in an ophthalmic lens configured to improve peripheral vision for a patient's eye. The lens comprises an optic with a first surface configured to receive ambient light, a second surface opposite the first surface and a peripheral region connecting the first and the second surfaces, wherein the optic is configured to focus an image at a peripheral retinal location disposed at a distance from the fovea. The lens further comprises a haptic comprising at least a first arm comprising a first end coupled with a first location of the optic and a second arm comprising a first end coupled with a second location of the optic, the first arm extending radially and anteriorly away from the first location, the second arm extending radially and anteriorly away from the second location, the first arm having a first length 11 and disposed at a first angle α1 with respect to a transverse axis of the optic perpendicular to the optical axis and passing through the first location, the second arm having a second length 12 disposed at a second angle α2 with respect to a transverse axis of the optic perpendicular to the optical axis and passing through the second location. The lens further comprises a contact member having a proximal end coupled to the second surface of the optic and a distal end configured to contact an existing lens in the eye of the patient. Each of the first and second arm comprises a second end configured to brace against an ocular structure and when so braced to position the attachment member in contact with the existing lens and displace the existing lens posteriorly in the eye by a distance d, the distance d being functionally dependent on the first angle α1 and the second angle α2.

In various embodiments of the ophthalmic lens the first length 11 can be equal to the second length 12. In some embodiments of the ophthalmic lens the distance d can be less than or equal to the first length 11. In some embodiments, the first length 11 can be greater than or equal to about 3.5 mm and less than or equal to about 5.0 mm. In various embodiments, the second length 12 can be greater than or equal to about 3.5 mm and less than or equal to about 5.0 mm. In various embodiments, the first angle α1 can be equal to the second angle α2. In various embodiments, the first angle α1 can be greater than or equal to about 15 degrees and less than or equal to about 45 degrees. The second angle α2 can be greater than or equal to about 15 degrees and less than or equal to about 45 degrees. The second surface of the optic can be configured to be spaced away from the anterior face of the existing lens at the central optical axis of the existing lens when the contact member is in contact with the existing lens. The optic can comprise an anterior portion and a posterior portion, the posterior portion comprising the second surface of the optic. The posterior portion can comprise a soft material configured to be in contact with the anterior face of the existing lens at a central optical axis thereof when the contact member is in contact with the existing lens. The contact member can comprise a rigid ring disposed within a body of the optic. The image can be produced by light incident on the patient's eye in an angular range between about 1 degree and about 50 degrees with respect to the optical axis.

BRIEF DESCRIPTION OF THE DRAWINGS

The systems, methods and devices may be better understood from the following detailed description when read in conjunction with the accompanying schematic drawings, which are for illustrative purposes only. The drawings include the following figures:

FIG. 9A illustrates a top view of an embodiment of an existing IOL comprising an optic and a haptic system.

FIG. 9B illustrates a cross-sectional view of a piggyback lens attached to the IOL illustrated in FIG. 9A.

FIG. 9A-1 illustrates a top view of an embodiment of an existing IOL comprising an optic and a haptic system, with an annular structure which is contiguous and completely surrounds the optic.

FIG. 9B-1 illustrates a cross-sectional view of a piggyback lens attached to the IOL illustrated in FIG. 9A-1.

FIG. 9C-1 illustrates a partial cross-sectional view of an embodiment of an IOL comprising an anterior surface that includes a central portion and a peripheral region spaced apart from the central region by a recessed annular region.

FIG. 9D illustrates a top view of an embodiment of a piggyback lens.

FIG. 9E-1 depicts a side-view of a piggyback lens prior to implantation in the sulcus.

FIG. 9E-2 depicts a side-view of a piggyback lens after implantation in the sulcus.

FIG. 10A-1 illustrates the top view of an IOL positioned in the capsular bag of an eye.

FIG. 10A-2 depicts a side-view of the IOL inserted into a capsular bag via capsulorhexis during which only a part of the anterior portion of the capsular bag that overlaps with the optical portion of the IOL is removed and other portions of the capsular bag are left intact.

FIG. 10B-1 illustrates the top view of an IOL positioned in a capsular bag of an eye, portions of the capsular bag being removed to increase flexibility.

FIG. 10B-2 illustrates the side view of the IOL implanted in a capsular bag portions of which have been removed.

DETAILED DESCRIPTION

The present disclosure generally provides devices, systems, and methods for improving or optimizing peripheral vision by reducing peripheral aberrations. Peripheral aberrations is a broad term and is intended to have its plain and ordinary meaning, including, for example, aberrations which occur outside of the central visual field, such as from light directed to peripheral or high field angle retinal areas. Peripheral aberrations can include, for example and without limitation, spherical aberrations, astigmatism, coma, field curvature, distortion, defocus, and/or chromatic aberrations. As disclosed herein, improving or optimizing peripheral vision includes reducing peripheral aberrations while maintaining good on-axis visual quality, or good visual quality at or near the central visual field.

The terms "power" or "optical power" are used herein to indicate the ability of a lens, an optic, an optical surface, or at least a portion of an optical surface, to focus incident light for the purpose of forming a real or virtual focal point. Optical power may result from reflection, refraction, diffraction, or some combination thereof and is generally expressed in units of Diopters. One of ordinary skill in the art will appreciate that the optical power of a surface, lens, or optic is generally equal to the refractive index of the medium (n) of the medium that surrounds the surface, lens, or optic divided by the focal length of the surface, lens, or optic, when the focal length is expressed in units of meters.

As used herein, an IOL or a lens refers to an optical component that is configured to be implanted into the eye of a patient. The IOL or the lens comprises an optic, or clear portion, for focusing light, and may also include one or more haptics that are attached to the optic and serve to position the optic in the eye between the pupil and the retina along an optical axis. In various implementations, the haptic can couple the optic to zonular fibers of the eye. The optic has an anterior surface and a posterior surface, each of which can have a particular shape that contributes to the refractive properties of the IOL or the lens. The optic can be characterized by a shape factor that depends on the radius of curvature of the anterior and posterior surfaces and the refractive index of the material of the optic. The optic can include cylindrical, aspheric, toric, or surfaces with a slope profile configured to redirect light away from the optical axis and/or a tight focus.

The angular ranges that are provided for eccentricity of the peripheral retinal location (PRL) in this disclosure refer to the visual field angle in object space between an object with a corresponding retinal image on the fovea and an object with a corresponding retinal image at a peripheral retinal location (PRL).

Phakic and Pseudophakic Eyes

Figure 1:
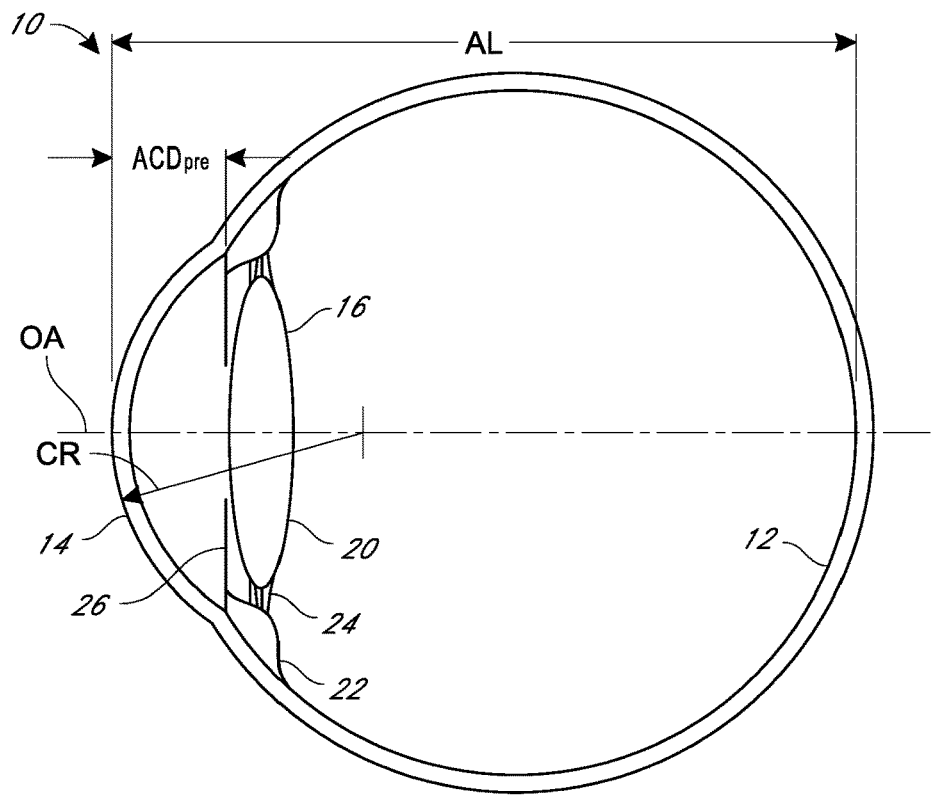
FIG. 1 is a cross-sectional view of a phakic eye containing a natural crystalline lens.

Embodiments disclosed herein may be understood by reference to FIG. 1, which is a cross-sectional view of a phakic eye with the natural crystalline lens, an eye 10 comprises a retina 12 that receives light in the form of an image that is produced by the combination of the optical powers of a cornea 14 and a natural crystalline lens 16, both of which are generally disposed about an optical axis OA. The eye has an axial length AL and a corneal radius CR. As used herein, an "anterior direction" is in the direction generally toward the cornea 14 relative to the center of the eye, while a "posterior direction" is generally in the direction toward the retina 12 relative to the center of the eye.

The natural lens 16 is contained within a capsular bag 20, which is a thin membrane that completely encloses the natural lens 16 and is attached to a ciliary muscle 22 via zonules 24. An iris 26, disposed between the cornea 14 and the natural lens 16, provides a variable pupil that dilates under lower lighting conditions (mesopic or scotopic vision) and contracts under brighter lighting conditions (photopic vision). The ciliary muscle 22, via the zonules 24, controls the shape and position of the natural lens 16, which allows the eye 10 to focus on both distant and near objects. Distant vision is provided when the ciliary muscle 22 is relaxed, wherein the zonules 24 pull the natural lens 16 so that the capsular bag 20 is generally flatter and has a longer focal length (lower optical power). Near vision is provided as the ciliary muscle contracts, thereby relaxing the zonules 24 and allowing the natural lens 16 to return to a more rounded, unstressed state that produces a shorter focal length (higher optical power).

The optical performance of the eye 10 also depends on the location of the natural lens 16. This may be measured as the spacing between the cornea 14 and the natural lens which is sometimes referred to as the anterior chamber depth prior to an ocular surgical procedure, ACDpre.

Figure 2:
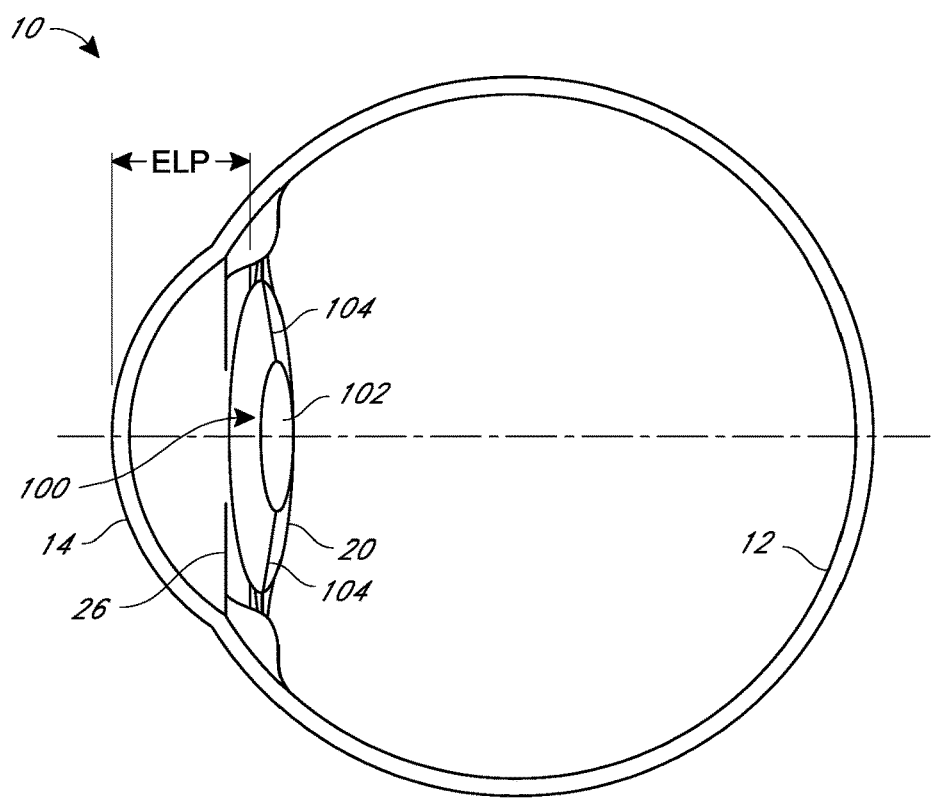
FIG. 2 is a cross-sectional view of a pseudophakic eye containing an intraocular lens.

Referring additionally to FIG. 2, which is a cross-sectional view of a pseudophakic eye 10, the natural crystalline 16 lens has been replaced by an intraocular lens 100. The intraocular lens 100 comprises an optic 102 and haptics 104, the haptics 104 being generally configured to position the optic 102 within the capsular bag 20, where ELP refers to the actual lens position. For purposes of the embodiments disclosed herein, the location of the intraocular lens is measured as the spacing between the iris and the anterior surface of the lens. A lens can have a principal plane that is at a distance, P, behind the anterior lens surface. For such a lens, where the disclosure refers to a distance, L, of the anterior surface of the lens of behind the iris, the principal plane of the lens is a distance P+L behind the iris. To provide example values, where the principal plane is about 0.4 mm behind the anterior lens surface and the lens is about 1.5 mm behind the iris, the principal plane of the lens would then be about 1.9 mm behind the iris. As discussed above, the location of the principal plane of the lens can vary depending on the shape factor of the IOL. Accordingly, for embodiments of lenses with different shape factors, the principal plane can be located at a distance different from 0.4 mm from the anterior surface of the lens.

Various standard IOLs available in the market are configured to improve on-axis optical image quality or improve quality of central vision when implanted in the eye such that the anterior surface of the standard IOL less than or equal to about 1 mm behind the iris. However, the optical image quality provided by the standard IOLs at a peripheral retinal location may be degraded. The peripheral retinal location (PRL) may be characterized by a PRL angle which is the angle between an imaginary axis passing through the iris and the PRL and the optical axis passing through the iris and the fovea. Optical image quality in the presence of significant aberrations, such as, for example, at peripheral retinal locations can be measured using the area under the modulation transfer function (AUMTF) up to a neurally determined cutoff limit. The cutoff limit can be determined using principles and methods described in C "Topography of ganglion cells in the human retina," by A. Curcio and K. A. Allen in J. Comp. Neurol., 300(1):5-25, 1990 which is incorporated by reference herein. MTF describes the contrast transfer function of the optical system as a function of spatial frequency of the object being viewed. The AUMTF curve is obtained by integrating the MTF at different spatial frequencies and for different view angles corresponding to different orientations of the eye. Without relying on any particular theory, for foveal vision, the reciprocal of the AUMTF curve can be well correlated with visual acuity. Accordingly, the reciprocal of the AUMITF curve can also be used as a metric for optical image quality at various PRLs.

Figure 3:
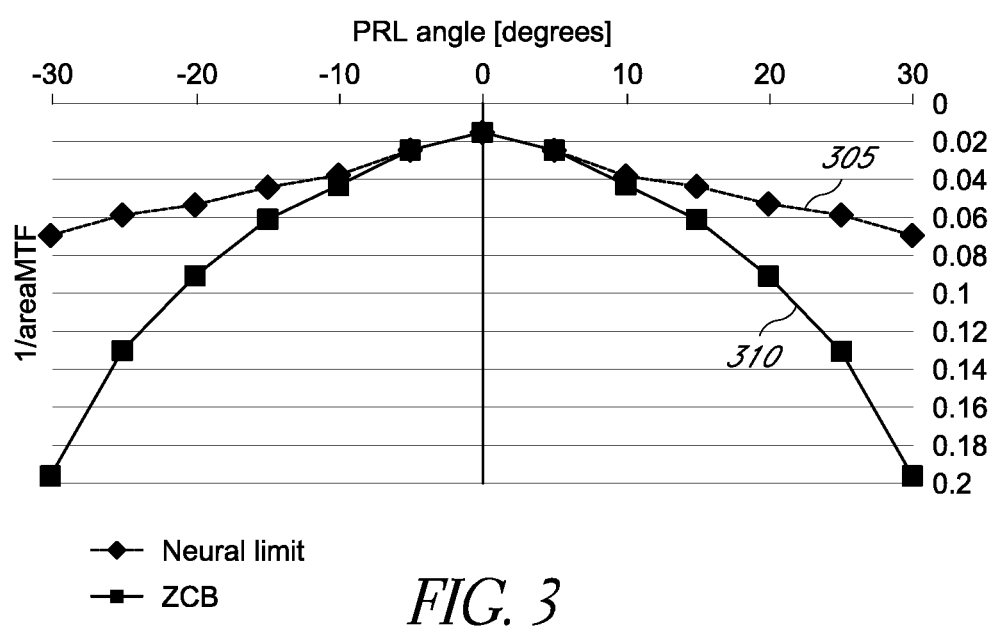
FIG. 3 illustrates a comparison of the optical image quality in the periphery of an eye implanted with different IOL configurations and the neural limit of the optical image quality in the periphery of an eye.

FIG. 3 illustrates the variation of the reciprocal of the area under the modulus transfer function (MTF) curve, which provides a measure of the optical image quality at various PRLs characterized by PRL angles between 0 degrees and ±30 degrees. It is observed from FIG. 3 that the optical image quality for a standard IOL, such as, for example, a toric IOL configured to provide on axis (foveal) refractive correction angle represented by curve 310 for a PRL angle between ±10 degrees and ±30 degrees is lesser than the neural limit for optical image quality at those PRLs represented by curve 305.

Placement of the Principal Plane of an IOL

In various embodiments described herein, the principal plane of the existing IOL is moved posteriorly or closer to the nodal point of the eye as compared to location of the principal plane of many standard IOLs currently being implanted. Without subscribing to any particular theory, displacing the IOL posteriorly can improve peripheral vision by reducing peripheral aberrations. A reason as to why pushing the existing IOL further into the eye reduces peripheral errors can be understood from the following optical theory. Aberrations of a lens depend on shape factor (X) and conjugate factor (Y). For example, spherical aberration functionally depends on the shape factor (X) and the conjugate factor (Y) as described in equation (1):

$$\sigma_1 = AX^2 + BXY + CY^2 + D \quad (1)$$

As another example, coma functionally depends on the shape factor (X) and the conjugate factor (Y) as described in equation (2):

$$\sigma_{11} = EX + FY \quad (2)$$

In general, oblique astigmatism $\sigma_{111}$ is equal to 1. Coma and oblique astigmatism can vary depending on displacement. For example, coma for an IOL disposed at a distance s from the pupil can be obtained from equation (3a) below and astigmatism for an IOL disposed at a distance s from the pupil can be obtained from equation (3b)

$$\sigma_{11}' = \sigma_{11} + \tau\sigma_1 \quad (3a)$$

$$\sigma_{111}' = \sigma_{111} + 2\tau\sigma_{11} + \tau^2\sigma_1 \quad (3b)$$

In equations 1, 2, 3a and 3b above, $$A = \frac{n+2}{n(n-1)^2}, B = \frac{4(n+1)}{n(n-1)^2}, C = \frac{3n+2}{n}, D = \frac{n^2}{(n-1)^2},$$

$$E = \frac{n+1}{n(n-1)}, F = \frac{2n+1}{n}, \text{ and } \tau = \frac{Fs}{(1-Y)Fs-2},$$

wherein n is the index of refraction, s the distance between pupil and IOL, F the power of the IOL, Y the conjugate factor and X the shape factor. As index of refraction, power, shape factor and conjugate factor cannot be changed, changing the distance s is the only parameter remaining to change for reducing peripheral errors.

In various embodiments, described herein, the principal plane of an existing IOL can be displaced posteriorly mechanically by applying a force along a direction parallel to the optical axis OA. In various embodiments, the existing IOL can be moved or displaced posteriorly by a distance, 'd', between about 0.5 mm to about 5.0 mm from its original location mechanically by the application of force. For example, the existing IOL can be displaced posteriorly from its original position by a by a distance, 'd' greater than or equal to about 0.5 mm and less than or equal to about 1.25 mm, greater than or equal to about 1.0 mm and less than or equal to about 1.75 mm, greater than or equal to about 1.5 mm and less than or equal to about 2.25 mm, greater than or equal to about 2.0 mm and less than or equal to about 2.75 mm, greater than or equal to about 2.5 mm and less than or equal to about 3.25 mm, greater than or equal to about 3.0 mm and less than or equal to about 3.75 mm, greater than or equal to about 3.5 mm and less than or equal to about 4.5 mm, or values therebetween.

Figure 4:
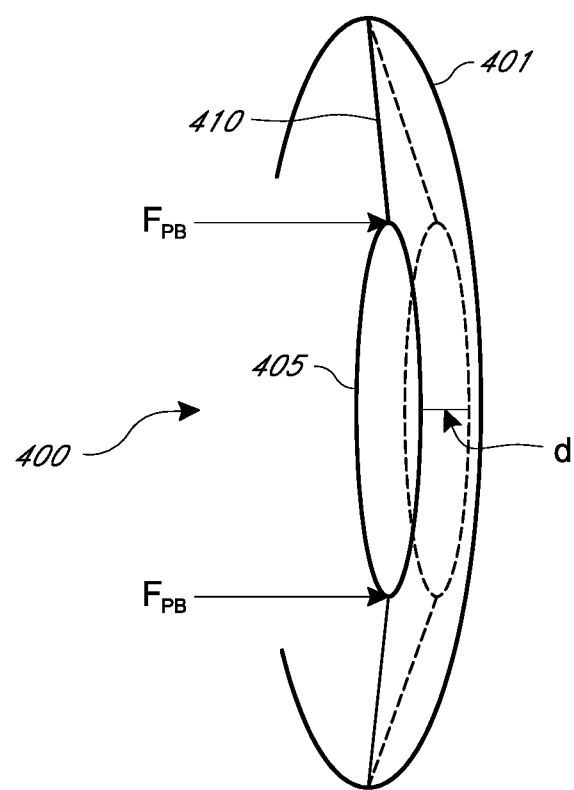
FIG. 4 illustrates an embodiment of an IOL placed in a capsular bag.

FIG. 4 illustrates an embodiment of an IOL 400 placed in a capsular bag 401. The IOL 400 comprises an optic 405 and a haptic 410. In various embodiments, the IOL 400 can be placed in the capsular bag 401 such that the anterior surface of the optic is less than about 1.0 mm from the iris. After implantation of the IOL, if it is determined that it is advantageous to displace the principal plane of the IOL posteriorly to improve foveal and/or peripheral image quality, then the optic 405 can be pushed rearward towards the retina by application of mechanical force $F_{PB}$. The mechanical force $F_{PB}$ can be provided by a piggyback lens that is implanted in the eye. The piggyback lens can be implanted in the capsular bag or in the sulcus. Moving the existing IOL posteriorly by implanting a piggyback lens that is configured to push the existing IOL away from the iris towards the retina such that the principal plane of the existing IOL is shifted by a desired distance, 'd' can advantageously reduce peripheral such that the IOL system including the existing IOL and the piggyback lens has reduced peripheral aberrations to improve optical image quality at a peripheral retinal location (PRL). In various embodiments, the distance, 'd' by which the existing IOL is displaced can be determined based on the material and optical properties of the existing IOL, the PRL angle and the amount of refractive and/or astigmatic correction desired at that PRL angle.

The existing IOL can be pushed rearward toward the retina by a desired distance when the piggyback lens is implanted in the eye. After the existing IOL is pushed to its desired axial location (e.g., by a distance 'd' from its original axial location), the connections between the add-on lens and the existing IOL in conjunction with the structure and material properties of haptic systems of the existing IOL and the piggyback lens can be relied upon to maintain the existing IOL at its desired axial location.

Implanting the piggyback lens to push the existing IOL away from the iris by a desired distance, 'd', can have several advantages. For example, implanting a standard IOL can bring substantial benefits to a patient suffering from cataracts and/or AMD. It is therefore possible that a surgeon would want to first try implanting a standard IOL in a patient suffering from cataracts and/or AMD and then consider extra treatment if the visual results of the first operation are unsatisfactory. As another example, while comorbidity of AMD and cataract is relatively common, a large group of patients can develop AMD long after cataract surgery. In such patients, the piggyback lens can improve the optical image quality at a peripheral retinal location of the existing lens by displacing the existing IOL rearward and simultaneously provide additional optical benefits. Furthermore, if a piggyback lens is implanted in conjunction with a standard IOL, then the range of refractive power provided by the piggyback lens can be reduced, this can advantageously limit the number of stock keeping units of the piggyback lenses.

Optical Profile of the Piggyback Lens to Improve Peripheral Image Quality

The piggyback lens that is used to push the existing IOL rearward towards the retina can include an optic and a haptic system. The optical image quality at a peripheral retinal location can be improved by configuring the optical profile of the optic of the piggyback lens to provide a desired visual quality in conjunction with the displaced existing IOL. The optical profile can be determined such that the optical power of the optic of the piggyback lens compensates for the change in the optical power resulting from the displacement of the existing IOL. The optical profile of the optic of the piggyback lens can also be configured to correct any residual refractive errors that were not corrected by the existing IOL including but not limited to astigmatism. In various embodiments, to advantageously reduce the number of stock keeping units, the range of optical power provided by the optic of the piggyback lens can be low, such as, for example, between about −5.0 D and about +5.0 D.

In addition to the correcting optical power, the optic of the piggyback lens can also at least partially correct some peripheral aberrations (e.g., aberrations arising due to oblique incidence of light) and thus improve optical image quality at the peripheral retinal location. For example, in some embodiments, the optic of the piggyback lens can have a meniscus shape and/or have a surface including higher order aspheric terms to improve optical image quality at the peripheral retinal location. For example, the anterior (that faces the cornea) and/or posterior surface (that faces the retina) of the optic of the piggyback lens can be mathematically described by a polynomial function represented by equation (4) below:

$$z = \frac{cr^2}{1 + \sqrt{1-(1+k)c^2r^2}} + \sum_{i=1}^{8} \alpha_i r^{2i} + \sum_{i=1}^{N} A_i Z_i(\rho, \phi) \quad (4)$$

where z is the sag of the surface, c is the curvature of the surface, r the radial distance from the optical axis of the optic of the piggyback lens, k the conic constant, a the aspheric coefficients, A are the Zernike coefficients and Z are the Zernike polynomials. In various embodiments, the anterior and/or posterior surface can be described by aspheric coefficients including upto the tenth order aspheric coefficients. In some embodiments, the anterior and/or posterior surface can be described by aspheric coefficients including aspheric coefficients with order less than ten (e.g., 2, 4, 6 or 8). In some embodiments, the anterior and/or posterior surface can be described by aspheric coefficients including aspheric coefficients with order greater than ten (e.g., 12 or 14). Alternatively, the anterior and/or posterior surface can be described by up to 34 Zernike polynomial coefficients. In some embodiments, the anterior and/or posterior surface can be described by less than 34 Zernike coefficients. In some embodiments, the anterior and/or posterior surface can be described by more than 34 Zernike coefficients. Additionally, the anterior and/or posterior surface can be described as a combination of these aspheric and Zernike coefficients. Examples of such embodiments were described in U.S. patent application Ser. No. 14/644,107, filed on Mar. 10, 2015; U.S. patent application Ser. No. 14/692,609, filed on Apr. 21, 2015; and U.S. patent application Ser. No. 14/849,369, filed on Sep. 9, 2015, all of which are incorporated by reference herein.

Various embodiments of the piggyback lens can be rotationally symmetric about the optical axis of the optic of the piggyback lens (or the optical axis, OA, of the eye when the piggyback lens is implanted in the eye such that the optical axis of the optic of the piggyback lens is aligned with the optical axis, OA, of the eye) such that a patient suffering from AMD who does not have a well-developed peripheral retinal location (PRL) can view objects by orienting his/her head along a direction that provides the best visual quality. Alternately, the piggyback lens can be rotationally asymmetric about the optical axis of the optic of the piggyback lens (or the optical axis, OA, of the eye when the piggyback lens is implanted in the eye such that the optical axis of the optic of the piggyback lens is aligned with the optical axis, OA, of the eye) such that a patient suffering from AMD who has a well-developed peripheral retinal location (PRL) can view objects by orienting his/her head along a direction that focuses light at the PRL. The piggyback lens can be sufficiently thin such that it can be placed in the space between the iris and the existing IOL. For example, the piggyback lens can have a thickness e.g. between 0.3 and 1.0 mm. The piggyback lens can be configured such that the area under the MTF curve provided by the combination of the existing IOL and the piggyback lens is above a threshold value for PRL angles between ±30 degrees of with only limited loss of foveal performance.

Figure 5:
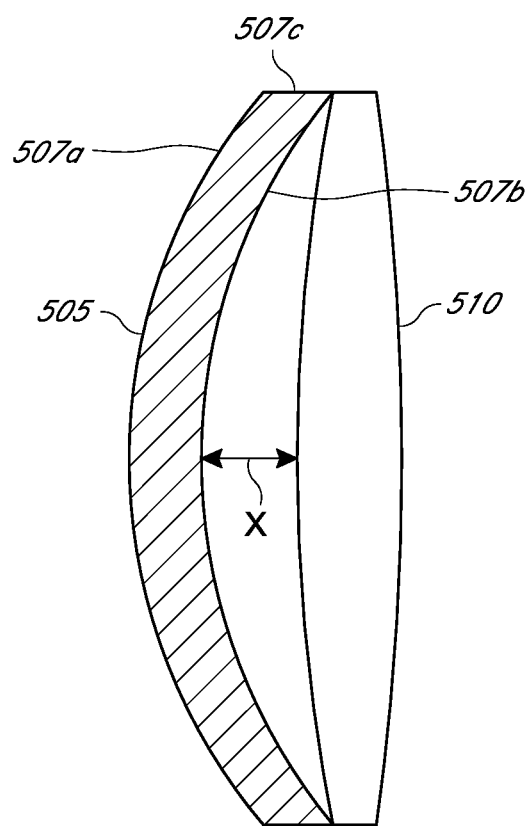
FIGS. 5-7 illustrate various embodiments of a piggyback lens that is positioned adjacent to an existing IOL.
Figure 6:
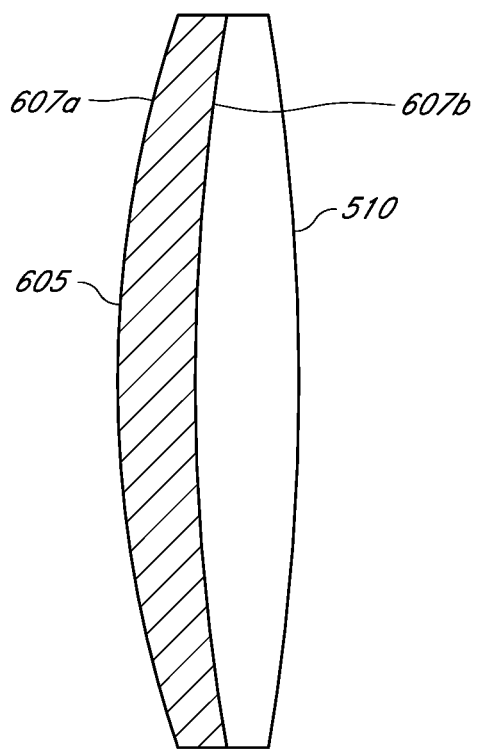
Figure 7:
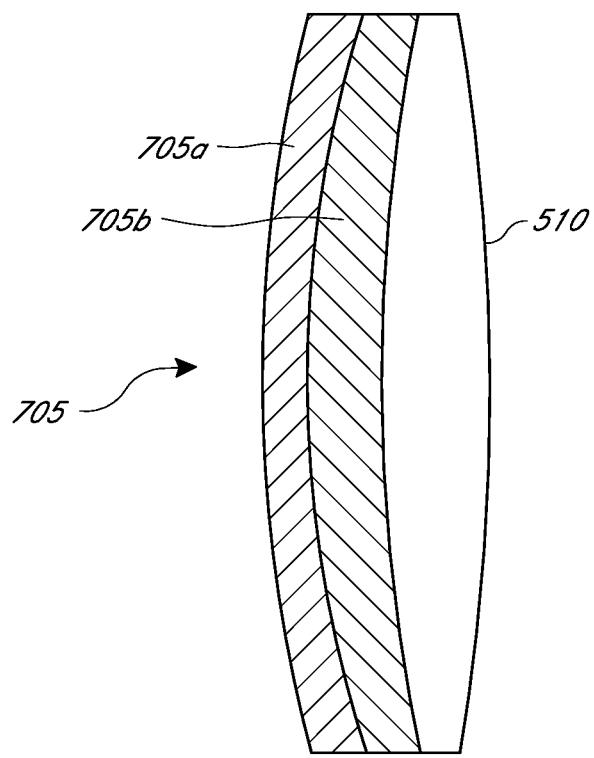

FIGS. 5-7 illustrate various embodiments of a piggyback lens that is positioned adjacent to an existing IOL 510. In various embodiments, the existing IOL 510 can be the SENSAR™ AR40 with OptiEdge™ lens sold by Abbot Medical Optics. In various embodiments, the existing IOL 510 can comprise materials including but not limited to silicone polymeric materials, acrylic polymeric materials, hydrogel polymeric materials, such as polyhydroxyethylmethacrylate, polyphosphazenes, polyurethanes, and mixtures thereof and the like. In some embodiments, the existing IOL 510 can comprise SENSAR® brand of acrylic. In various embodiments, the surface of the existing IOL 510 can comprise materials such as, for example, heparin, PEG/SiO2 or other materials that can be impervious to water, blood, or other body fluids. In various embodiments, portions of the existing IOL 510 (e.g., the edges or peripheral portions) can be masked by a light blocking material to create an additional IOL. In various embodiments, portions of the surfaces of the existing IOL 510 can be textured (e.g., the edges of the surfaces of the existing IOL 510 can be frosted). In various embodiments, the existing IOL 510 can comprise a high refractive index material. Lenses comprising higher refractive index material can be thinner than lenses comprising a lower refractive index material.

The embodiments of piggyback lenses illustrated in FIGS. 5-7 are meniscus lenses having anterior surface that receives ambient light being convex and a posterior surface opposite the anterior surface being concave. A meniscus piggyback lens can be thicker at the center than at the edges. The meniscus lens may be configured to reduce distortion in the image quality caused by edge effects. Various other embodiments of piggyback lenses need not be meniscus lenses but can include bi-convex lenses, concave lenses, plano-convex lenses, etc. In various embodiments, the piggyback lens can be spaced apart from the existing IOL 510 in a central optical zone such that the piggyback lens and the existing do not touch each other at the optical vertex. Such an arrangement is illustrated in FIG. 5 which depicts a piggyback lens 505 having an anterior surface 507a and a posterior surface 507b disposed forward of an existing IOL 510. The anterior surface 507a and the posterior surface 507b can meet at a peripheral region 507c (e.g., at a peripheral edge). In various embodiments, the peripheral region 507c can be a portion of the circumference of the piggyback lens 505. As illustrated in FIG. 5, the posterior surface 507b of the piggyback lens 505 is spaced apart from the anterior surface of the existing IOL 510 in a central region such that the piggyback lens 505 contacts the existing IOL 510 in a peripheral region of the existing IOL 510. In the embodiment illustrated in FIG. 5, the posterior surface 507b of the piggyback lens 505 is spaced apart from the vertex of the existing IOL 510 by a distance, x. Spacing the piggyback lens 505 from the existing IOL 510 at least in the region around the vertex of the existing IOL 510 can advantageously prevent cell growth as well as flattening at the optical vertex.

FIG. 6 illustrates an embodiment of a piggyback lens 605 comprising a soft material with a low refractive index. The piggyback lens 605 comprises an anterior surface 607a and a posterior surface 607b. Such an embodiment of a piggyback lens is configured to provide the desired mechanical force $F_{PB}$ to displace the existing IOL 510 posteriorly towards the retina by a desired distance while maintaining the optical power of the existing IOL 510 substantially the same. For example, the material of the piggyback lens 605 can have a refractive index that changes the optical power of the existing IOL 510 by no more than about 10% such that the optical power of the existing IOL 510 remains substantially the same. The Young's modulus (E) of the optic body material of the piggyback lens 605 can be about 10% of the Young's modulus of the material of the existing IOL 510. The posterior surface 607b of the embodiment of the piggyback lens 605 illustrated in FIG. 6 can have a shape similar to or the same as the shape of the anterior surface of the existing IOL 510 so that the posterior surface 607b of the piggyback lens 605 can contact the anterior surface of the existing IOL 510. This can reduce interlenticular opacification and reflections or ghost images. For example, in various embodiments, the shape of the posterior surface of the piggyback lens 605 can be configured to match the anterior surface of the existing IOL 510.

FIG. 7 illustrates an embodiment of a piggyback lens 705 comprising an outer portion 705a and an inner portion 705b. The outer portion 705a can comprise a material that is similar to the material of the existing IOL 510, such as, for example, hydrophobic acrylic. The outer portion 705a can include a material having a refractive index that is similar to the refractive index of the existing IOL. For example, a difference between the refractive index of the material of the outer portion 705a and the refractive index of the material of the existing IOL 510 can be ±10%. The inner portion 705b can comprise a soft material having a refractive index that is lower than the refractive index of the material of the outer portion 705a (and/or the refractive index of the material of the existing IOL 510). For example, the refractive index of the material of the inner portion 705b can be between about 1% to about 20% lower than the refractive index of the material of the outer portion 705a. The Young's modulus (E) of the soft material of the inner portion 705b can be about 10% of the Young's modulus (E) of the material of the existing IOL 510 and/or the material of the outer portion 705a. In various embodiments, the inner portion 705b comprising the soft material can be disposed adjacent to the existing IOL 510 and the outer portion can be disposed to receive incident ambient light. The posterior surface of the inner portion 705b can have a shape similar to the shape of the anterior surface of the existing IOL 510 so that the posterior surface of the inner portion 705b can contact the anterior surface of the existing IOL 510 with reduced interlenticular opacification and reflections or ghost images. For example, in various embodiments, the shape of the posterior surface of the inner portion 705b can be configured to match the anterior surface of the existing IOL 510. In various embodiments, the optical, structural and material properties of the outer portion 705a can be similar to the optical, structural and material properties of the piggyback lens 505. In various embodiments, the optical, structural and material properties of the outer portion 705b can be similar to the optical, structural and material properties of the piggyback lens 605.

Figure 8A:
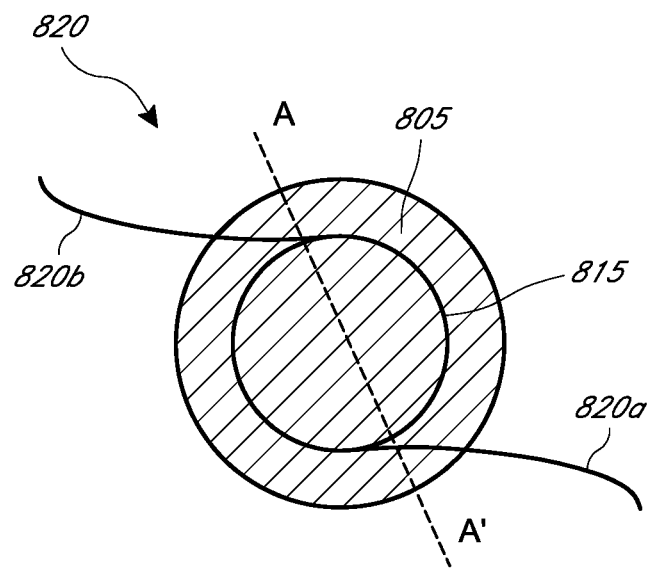
FIG. 8A illustrates a top view of a piggyback lens comprising a soft material.
Figure 8B:
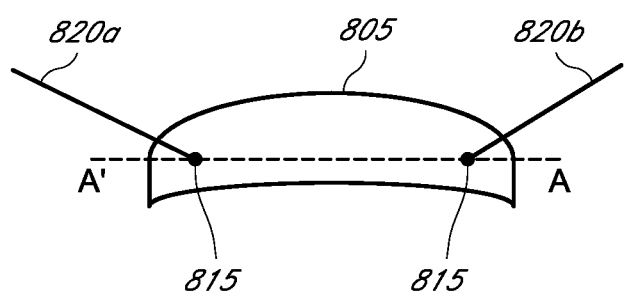
FIG. 8B illustrates a side view of the piggyback lens illustrated in FIG. 8A.

In various embodiments, the optic of a piggyback lens configured to push the existing IOL posteriorly towards the retina can be disposed around a frame that provides structural support to the optic. A frame that provides structural support can advantageously provide structural support to a piggyback lens that comprises a soft material (e.g., piggyback lens 605). In various embodiments, the frame can also be configured as a posterior displacer to push the existing IOL posteriorly towards the retina. In various embodiments, the frame can comprise an anchor system that is configured to anchor the piggyback lens in the eye. Such an embodiment is illustrated in FIGS. 8A and 8B. FIG. 8A illustrates an optic 805 of a piggyback lens that is disposed around a frame comprising an annular structure 515b and an anchor system including a plurality of anchor arms 515a. For example, the optic 805 can be cast around the frame. FIG. 8B is a cross-sectional view of optic 805 along the axis A-A'. In various embodiments, the annular structure 515b can comprise a ring shaped structure as shown in FIG. 8A. In some embodiments, the annular structure 515b can be discontinuous. The anchor arms 515a include a first end that is coupled to the piggyback lens 805 and a second free end that is configured to be connected to an anatomy of the eye (e.g., sulcus or ciliary body). In various embodiments, the anchor arms 515a extend radially outward from the optic 805 as shown in FIGS. 8A and 8B. The first end of the anchor arms can be coupled to the annular structure 515b as illustrated in FIGS. 8A and 8B. Alternately, a first end of the anchor arms 515a can be attached to the optic 805 at a region that is distinct from the annular structure 515b. Various features of the frame including a central ring 515b and one or more anchor arms 515a illustrated in FIGS. 8A and 8B can be similar to the haptic systems discussed below.

The optical characteristics (e.g., characteristics of the anterior and/or posterior surfaces, radius of curvature of the anterior and/or posterior surfaces, asphericity of the anterior and/or posterior surfaces) of various embodiments of piggyback lenses (e.g., piggyback lens 505, piggyback lens 605, piggyback lens 705, optic 805) disclosed herein can be determined based on dimensions of an average eye. For example, the characteristics of the optical surface of the piggyback lens 505 can be determined based on the average axial length (AL), average corneal radius (CR), average anterior chamber depth (ACD) and average horizontal corneal diameter. In some embodiments, diagnostics specific to a patient's eye can be obtained, such as, for example, corneal power and asphericity, retinal curvature, PRL location and/or anterior chamber depth and the optical characteristics of the piggyback lens 505 can be determined based on the obtained diagnostics. In some embodiments, various embodiments of piggyback lenses (e.g., piggyback lens 505, piggyback lens 605, piggyback lens 705, optic 805) disclosed herein can include a diffractive optical element to provide correction for chromatic aberrations. The optical characteristics of various embodiments of piggyback lenses (e.g., piggyback lens 505, piggyback lens 605, piggyback lens 705, optic 805) disclosed herein and/or the displacement distance of the existing IOL 510 can be optimized using different merit functions, such as, for example, area under the modulation transfer function (MTF) curve obtained for different spatial frequencies, area under the weighted MTF calculated for different defocus positions which can be calculated by the area under the product of the neural contrast sensitivity (as measured by Campbell and Green in 1965) and the MTF measured in the optical bench for a range of spatial frequencies, area under the weighted optical transfer function given by the function MTF*cos(PTF)*nCSF for a range of spatial frequencies, wherein PTF is the phase transfer function measured in the optical bench and the nCSF the neural constrast sensitivity as measured by Green and Campbell (1965) and/or the cross correlation (X-cor) metric that is obtained by performing a convolution of a reference image and the image collected by a bench-top optical system for each defocus position, adjusting parameters of the collected image, such as for example, magnification, average intensity levels and position shifts of the collected images in order to yield the highest cross correlation coefficient.

In some embodiments, the optical characteristics of the various embodiments of piggyback lenses (e.g., piggyback lens 505, piggyback lens 605, piggyback lens 705, optic 805) disclosed herein and/or the displacement distance of the existing IOL 510 can be optimized using a metric that is estimated from preclinical measurements by the area under the through focus MTFa (AU MTFa) for a given spatial frequency range (e.g. from 0 cycles per mm to 50 cycles per mm; from 0 cycles per mm to 100 cycles per mm). The AU MTFa, calculated from the preclinical through focus MTF measurements can provide a single value to describe the average visual performance of a pseudophakic patient implanted with an IOL over a range of defocus.

In some embodiments, the optical characteristics of the various embodiments of piggyback lenses (e.g., piggyback lens 505, piggyback lens 605, piggyback lens 705, optic 805) disclosed herein and/or the displacement distance of the existing IOL 510 can be optimized using a metric that is based on the area under the through focus wMTF (AU wMTF) for that defocus range. The AU wMTF can be calculated by integrating the wMTF over a defocus range (e.g. between −2 D and −0.5 D to evaluate intermediate vision).

In some embodiments, the optical characteristics of the various embodiments of piggyback lenses (e.g., piggyback lens 505, piggyback lens 605, piggyback lens 705, optic 805) disclosed herein and/or the displacement distance of the existing IOL 510 can be optimized using a metric that is based on the area under the through focus (AU wOTF) for that defocus range. The AU wOTF can be calculated by integrating the wOTF over a defocus range (e.g. between −2 D and −0.5 D to evaluate intermediate vision).

In some embodiments, the optical characteristics of the piggyback IOL 505 and/or the displacement distance of the existing IOL 510 can be optimized using a metric that is based on the area under the through focus X-cor (AU X-cor) for that defocus range. The AU X-cor can be calculated by integrating the X-cor curve over a defocus range (e.g. between −2 D and −0.5 D to evaluate intermediate vision). The different metrics identified above are described in detail in U.S. application Ser. No. 14/878,294 filed on Oct. 8, 2015, entitled "Apparatus, Systems and Methods for Improving Visual Outcomes for Pseudophakic Patients," which is incorporated by reference herein and made part of this application.

For some patients, various embodiments of piggyback lenses (e.g., piggyback lens 505, piggyback lens 605, piggyback lens 705, optic 805) disclosed herein can be implanted along with the existing IOL 510 during the same surgical procedure. In such patients, a measurement of peripheral error can be obtained during the surgery and a piggyback lens having optical characteristics that can reduce or eliminate the peripheral error can be selected for implantation. In various embodiments, the piggyback lens need not provide any optical correction or improvement but can be configured to only provide the mechanical force $F_{PB}$ that is required to push the existing IOL 510 posteriorly towards the retina. In such embodiments, the piggyback lens can be configured zero (or no) spherical and/or cylindrical power.

Various embodiments of existing IOL's 510 can be configured to be expandable by providing structures that can facilitate implantation of piggyback lenses when, required. Such structures are disclosed below.

Connections Between the Piggyback Lens and the Existing IOL

In various embodiments, the piggyback lens can be mechanically connected with the existing IOL. Connections between the piggyback lens and the existing IOL can advantageously provide stability to the piggyback lens, the existing IOL and/or the combined piggyback lens and existing IOL. The connections between the piggyback lens and the existing IOL can also maintain the axial position of the existing IOL at the new displaced location and prevent the existing IOL from returning to its original location due to forces from various parts of the eye (e.g., vitreous humour, zonules, ciliary bodies, etc.). The connections between the piggyback lens and the existing IOL can advantageously maintain a desired inter-lenticular distance between the piggyback lens and the existing IOL. For example, in various embodiments, the piggyback lens can be held at a position that is spaced apart from the vertex of the existing IOL such that the piggyback lens and the existing IOL do not contact each other at the optical vertex. As discussed above, spacing the piggyback lens and the existing IOL such that they do not contact each other at the optical vertex can prevent cell growth as well as flattening at the vertex in some embodiments of a piggyback lens. The connections between the piggyback lens and the existing IOL can be configured to ensure a proper centration of both the piggyback lens and/or the existing IOL. In other words, the connections between the piggyback lens and the existing IOL can advantageously maintain the alignment between the optical axis of the optic of the piggyback lens and/or the existing IOL and the optical axis, OA of the eye. In various embodiments, the piggyback lens can be connected to the existing IOL in a peripheral region of the existing IOL. For example, in some embodiments, connections between the piggyback lens and the existing IOL can be made in a peripheral region of the existing IOL. Without any loss of generality, the peripheral region of the existing IOL can comprise a recessed annular region disposed at least partially along the periphery of the existing IOL. In various embodiments, the piggyback lens and the existing IOL can be locked in together using a ridge design. These and other concepts are discussed below with reference to FIGS. 9A-9C and 9C-1.

FIG. 9A illustrates a top view of an embodiment of an existing IOL 910 comprising an optic 901 and a haptic system 920 that holds the optic 901 in place when implanted in the eye. For example, in some embodiments, when implanted in the capsular bag 20 of the eye, the haptic system 920 can hold the optic 901 such that the principal plane of the optic is about 0.9 mm rearward of the iris. As another example, in some embodiments, when implanted in the capsular bag 20 of the eye, the haptic system 920 can hold the optic 901 such that the anterior surface of the optic 901 is about 0.5 mm rearward of the iris. The optic 901 can be a lens that provides refractive and/or astigmatic power correction for central vision. In various embodiments, the IOL 910 can be implanted in the eye of a patient after removal of the natural lens 16 during a cataract surgery. Alternately, the IOL 910 can be implanted in addition to the natural lens 16 to provide refractive or astigmatic power correction.

The haptic system 920 can comprise a biocompatible material that is suitable to engage the capsular bag of the eye, the iris 26, the sulcus and/or the ciliary muscles of the eye. For example, the haptic can comprise materials such as acrylic, silicone, polymethylmethacrylate (PMMA), block copolymers of styrene-ethylene-butylene-styrene (C-FLEX) or other styrene-base copolymers, polyvinyl alcohol (PVA), polystyrene, polyurethanes, hydrogels, etc. In various embodiments, the haptic system 920 can include one or more arms that are coupled to the optic 901. For example, the haptic system 920 can include arms 920a and 920b that radiate outward from the periphery optic 901. In various embodiments, one or more arms of the haptic system 920 can protrude into the optic 901. In various embodiments, the peripheral portions of the one or more arms of the haptic system 920 can be curved (e.g., hooked or having a C, S or J shape) so as to securely engage the capsular bag, the zonules, the ciliary bodies, the sulcus or any other anatomy of the eye which the haptics are configured to engage. In various embodiments, the one or more arms of the haptic system 920 can be curved in the plane of the optic 901. In some embodiments, the one or more arms of the haptic system 920 can be curved in a plane different from the plane including the optic 901.

In various embodiments, the haptic system 920 can be transmissive and have a transmissivity that is substantially equal to (e.g., within about 20%) of the transmissivity of the optic 901. In various embodiments, the material of the haptic system 920 can have a refractive index that is substantially equal to (e.g., within about 20%) of the refractive index of the material of the optic 901.

In various embodiments, the haptic system 920 can be configured to move the optic 901 along the optical axis of the eye in response to ocular forces applied by the capsular bag and/or the ciliary muscles. For example, the haptic system 920 can include one or more hinges to facilitate axial movement of the optic 901. As another example, the haptic system 920 can include springs or be configured to be spring-like to effect movement of the optic 901.

In various embodiments, the existing IOL 910 can also include a structure that helps maintain the centration and/or the orientation of the existing IOL 910 with respect to various anatomical structures and/or implanted structured in the eye. For example, as illustrated in FIG. 9A, an annular structure 925 can be disposed at least partially about the periphery of the optic 901 to maintain centration and/or the orientation of the existing IOL 910 with respect to various anatomical structures and/or implanted structured in the eye. In some embodiments, the annular structure 925 can be disposed external to the optic 901 such that the annular structure 925 completely or at least partially surrounds the optic 901. In some other embodiments, the annular structure 925 can be disposed internal to the optic 901. For example, the optic 901 can be cast or molded over the annular structure 925.

In some embodiments, as illustrated in FIGS. 9A-1 and 9B-1 the annular structure 925 can be contiguous and completely surrounds the optic 901. In some embodiments, the annular structure 925 can be broken at predetermined location. For example, in the embodiment illustrated in FIG. 9A, the annular structure 925 is discontiguous and comprises a first portion 925a and a second portion 925b. The portions 925a and 925b are spaced apart by gaps 928a and 928b. The gaps 928a and 928b between the two portions of the annular structure 925 overlap with region where the haptic arms 920a and 920b are attached to the optic 901. In such embodiments, the annular structure 925 and the haptic system 920 can be distinct and/or separate from each other. Alternately, in some embodiments, the annular structure 925 can be integrated with the haptic system 920 such that the annular structure 925 is a part of the haptic system 920. In various embodiments, the annular structure 925 can include grooves, pins, barbs, clips, etc. to facilitate attachment to the optic 901. In various embodiments, the annular structure 925 can include a locking or a fastening mechanism that facilitates attachment to the optic 901 and helps maintain the centration and/or orientation of the optic 901.

The annular structure 925 can be transmissive and have a transmissivity that is substantially equal to (e.g., within about 20%) of the transmissivity of the optic 901. The material of the annular structure 925 can have a refractive index that is substantially equal to (e.g., within about 20%) of the refractive index of the material of the optic 901. The annular structure can comprise a material having sufficient rigidity or stiffness to maintain desired centration and/or orientation of the optic 901. Without subscribing to any particular theory, the IOL 910 can be configured such that the surface moment of inertia for bending in a plane transverse to the plane of the optic 901 can be higher than the surface moment of inertia for bending in the plane of the optic 901. For example, consider an IOL having a rectangular cross-section. For such an IOL, the moment of inertia in a plane transverse to the plane of the IOL is given by the product $\frac{1}{12}*\text{width}*\text{height}^3$ and in the plane of the IOL is given by the product $\frac{1}{12}*\text{height}*\text{width}^3$. Accordingly, the axial stability will be higher if the height is greater than width.

FIG. 9B illustrates a cross-sectional view of a piggyback lens 905 attached to the IOL 910 illustrated in FIG. 9A. In the illustrated embodiments, the piggyback lens 905 comprises a posterior displacer 907 that extends posteriorly from the piggyback lens 905 and is configured to contact the existing IOL 910 and push the existing IOL 910 rearward from its original location to a displaced location. The posterior displace 907 can include one or more projections 917. The projections 917 of the posterior displacer can be configured to contact one or more portions of the existing IOL 910. Each projection 917 has a proximal end 919a that is coupled to the piggyback lens 905 and a distal end 919b that is configured to be connected to the peripheral region of the optic 901, the haptic system 920 and/or the annular structure 925. For example, the projections 917 can be configured to be connected to the annular structure 925 of the IOL 910. The annular structure 925 can include grooves on the portion that faces the projections 917 to facilitate attachment with the piggyback lens 905. The projections 917 can include protrusions that can be configured to engage the grooves in the annular structure 925. Locking mechanisms (e.g., clips, screws, etc.) can be used to secure the attachment between the piggyback lens 905 and the existing IOL 910. The projections 917 and the manner in which they are connected to the existing IOL 910 may be at least partially responsible in pushing the existing IOL 910 posteriorly to a displaced axial location and maintain the existing IOL 910 at the displaced axial location in presence of ocular forces exerted by different anatomical part of the eye (e.g., the posterior capsule, the vitreous humour).

Figures 1, 9C:
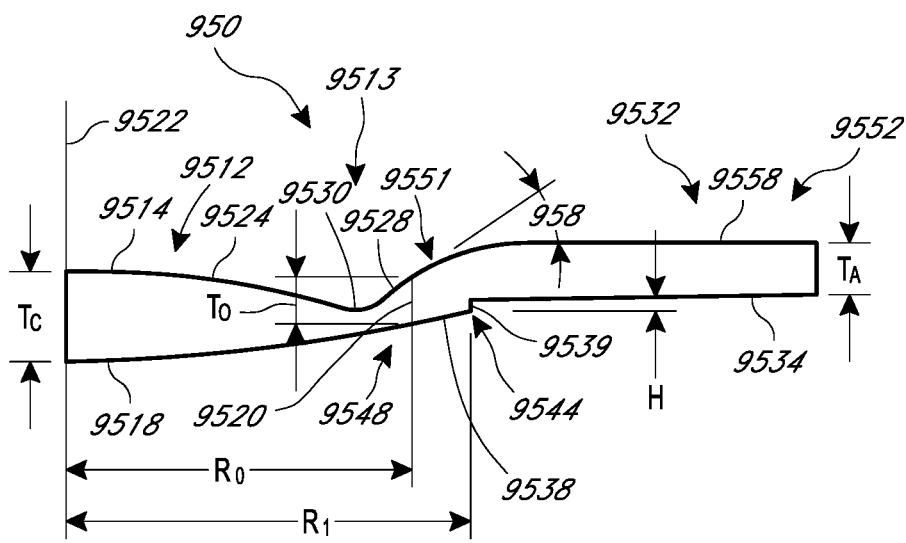
FIG. 9C illustrates a side-view of a piggyback lens attached to an embodiment of an IOL.

FIG. 9C illustrates a side-view of a piggyback lens 905 attached to an IOL 950. Various physical and optical features of the IOL 950 can be similar to the IOL 910 illustrated in FIG. 9A. FIG. 9C-1 depicts a partial cross-sectional view of an embodiment of an IOL 950 that is configured as a foldable intraocular lens comprising an optic 9511 including an optical zone 9512 and a peripheral zone 9513 surrounding the optical zone 9512. The optic 9511 has an anterior surface 9514, an opposing posterior surface 9518, and an optic edge 9520. The anterior surface 9514 and the posterior surface 9518 can be intersected by an optical axis 9522. The anterior surface 9514 can comprise a central portion 9524, a peripheral region 9528, and a recessed annular region 9530 disposed between the central portion 9524 and the peripheral region 9528.

The intraocular lens 950 can further comprise at least one haptic 9532 that is attached to the peripheral zone 9513. The haptic 9532 comprises a distal posterior surface 9534, a proximal posterior surface 9538, and a step edge 9539 disposed at a boundary therebetween. The haptic further comprises a side edge 9540 disposed between the optic edge 9520 and the step edge 9539. The proximal posterior surface 9538 and the posterior surface 9518 of the optic 9511 form a continuous surface 9548. An edge corner 9550 is formed by the intersection of the continuous surface 9548 with the optic edge 9520, the side edge 9540, and the step edge 9539. In various embodiments, the haptics 9532 can be integrated with the peripheral zone 9513. For example, the haptics 9532 can be monolithically integrated with the peripheral zone 9513. As another example, the haptics 9532 can be integrally formed with the peripheral zone 9513 and comprise the same material as the optic 9511 so as to form a one-piece IOL 950. Alternatively, the haptics 9532 may be integrally formed in a common mold with the optic 9511, but comprise a different material than the optic 9511. In other instances, the haptics 9532 can be formed of the same material as the optic 9511, but the material of the haptics 9532 and the optic 9511 can have different properties. For example, the haptics 9532 may have different tensile strength than the optic 9511. In yet other embodiments, the haptics 9532 may be formed separately from the optic 9511 and attached to the optic 9511 to provide a three-piece configuration.

The optical zone 9512 can have a center thickness Tc measured substantially along the optical axis 9522, that is in the range of about 0.5 mm or less to about 1.0 mm or more. For example, the center thickness Tc, can be in the range of about 0.7 mm to about 0.9 mm. The center thickness Tc, may vary depending on factors such as the lens material and the dioptric power of the optical zone 9512. The optic 9511 can have a diameter between about 4 mm to about 7 mm or more. For example, the diameter of the optic body can be between about 5 mm to about 6.5 mm or about 6.0 mm.

The haptics 9532 can be characterized by a haptic thickness T, that is equal to a distance, as measured along the optical axis 9522, between the distal posterior surface 9534 of the haptic 9532 and the opposing proximal posterior surface 9558. The haptic thickness T, can be greater than or approximately equal to a thickness To of the optic edge 9520, as measured along the optical axis 9522. The thicknesses T, and To may be selected based on the particular material from which the intraocular lens 950 is made, the amount of rigidity desired, the optical power of the lens 10, and other such factors. In various embodiments, at least one of the haptic thickness T, and the optic edge thickness To, can be in the range of about 0.2 mm or less to about 1 mm or more, in the range of about 0.3 mm to about 0.6 mm, or in the range of about 0.4 mm to about 0.5 mm The step edge 9539 is disposed between the proximal posterior surface 9538 and distal posterior face 9534 of each haptic 9532. The step edge 9539 can be a part of the edge corner 9550 that forms a continuous boundary around the posterior surface 9518 of the optic 9511. In certain embodiments, the step edge 9539 has a height H that is in the range of about 0.05 mm or less to about 1 mm or more, in the range of about 0.05 mm to about 0.2 mm. In other embodiments, the step edge 9539 can have a height H that is in the range of about 0.2 mm to about 0.5 mm.

In certain embodiments, at least a portion of the step edge 9539 can be a straight line and disposed at a radius $R_1$, from the optical axis 9522. Alternatively or additionally, at least a portion of the step edge 9539 may be arcuate in shape. The radius $R_1$, is advantageously greater than the radius $R_0$, of the optic edge 9520 so that a proximal portion of the haptic 9532 forms a buttress 9551 that is preferably thicker than a distal portion 9552 of the haptic 9532 and the edge thickness To.

The peripheral zone 9513 and the buttress 9551 can form a generally rigid structure, that allows the central portion 9524 to be recessed such that the recessed annular region 9530 of the peripheral zone 9513 is posterior to the peripheral region 9528. This recessed configuration of the central portion 9524, compared to an optic not having the recessed annular region 9530, can reduce the total volume of the intraocular lens 950 by reducing the overall thickness of the optical zone 9512. In certain embodiments, at least a portion of the peripheral region 9528 of the optic 9511 can be disposed at an angle θ relative to a plane perpendicular to the optical axis 9522. The angle θ can be in the range of about 5 degrees or less to at least about 50 degrees, depending on the dioptric power of the optical zone 9512 and the radius of curvature of the posterior surface 9518 and the central portion 9524 of the optical zone 9512. In some embodiments, the angle θ can be in the range between about 15 degrees to about 35 degrees. The IOL 950 can have features that are similar to embodiments of IOLs discussed in U.S. Pat. No. 8,382,832, titled "Foldable Intraocular Lens and Method of Making," which is incorporated herein by reference in its entirety.

In the illustrated implementation, the piggyback lens 905 can be configured to be attached to the peripheral region 9528 of the IOL 950. The projections 917 of a piggyback lens 905 that is configured to be supported by the peripheral region 9528 of the IOL 950 can include protrusions, pins, etc. that are configured to engage the peripheral region 9528 of the IOL 950. In another embodiment, the piggyback lens 905 can be configured to be attached to a projection or protrusion of the IOL 950. The protrusion can be configured as a ring-like projection or a plurality of spaced apart protrusion disposed about the periphery of the IOL 950. The projections 917 of a piggyback lens 905 that is configured to be supported by the peripheral region 9528 of the IOL 950 can include concave surfaces to receive the projection or projections.

In some embodiments, each projection 917 can comprise a notch 927. A first portion on one side of the notch 927 can be configured to be disposed along a peripheral region of the existing IOL 910 (e.g., a side portion) and a second portion on another side of the notch 927 can be configured to be disposed along an anterior surface of the existing IOL 910. The portion of the projection 917 that contacts the anterior surface of the existing IOL 910 and/or the peripheral region of the existing IOL 910 can be configured to have refractive index that is substantially similar (e.g., within ±20%) as the refractive index of the material of the anterior surface of the existing IOL 910 and/or the peripheral region of the existing IOL 910 so as to reduce optical distortion. The portion of the projection 917 that contacts the anterior surface of the existing IOL 910 and/or the peripheral region of the existing IOL 910 can be configured to have a surface shape that matches the shape of the anterior surface of the existing IOL 910 and/or the peripheral region of the existing IOL 910 so as to reduce surface discontinuities between the projection 917 and the existing IOL 910. In some embodiments, the portion of the projection 917 that contacts the anterior surface of the existing IOL 910 can comprise an anteriorly angled surface configured to mate with a posteriorly angled region of the anterior surface of the existing IOL 910. In some embodiments, the portion of the projection 917 that contacts the anterior surface of the existing IOL 910 can comprise a posteriorly angled face configured to mate with an anteriorly angled region of the anterior surface of the existing IOL 910. In various embodiments, the distal ends 919b of the plurality of the projections 917 can be connected together. For example, the distal ends 919b of the plurality of the projections 917 can be connected together by arcuate segments to form a ring shaped structure. In such embodiments, the ring shaped structure formed by connecting the distal ends 919b of the plurality of the projections 917 can be configured to be connected to the peripheral regions of the optic 901 (e.g., peripheral region 9528). In such embodiments, the ring shaped structure formed by connecting the distal ends 919b of the plurality of the projections 917 can include a stiff material that can resist ocular forces and maintain the desired centration, orientation and/or the axial position of the existing IOL 910. Accordingly, in such embodiments, the existing IOL 910 may not include the annular structure 925. In various embodiments, the proximal ends 919a of the plurality of attachments arms can be connected together by arcuate segments to form a ring shaped structure (e.g., the annular structure 515b illustrated in FIG. 8A). In such embodiments, the ring shaped structure formed by connecting the proximal ends 919a of the plurality of the projections 917 can provide structural stability to the piggyback lens 905. In various embodiments, one end of the haptic arms 916a and 916b can be connected to the proximal ends 919a of one or more of the projections 917.

The piggyback lens 905 illustrated in FIGS. 9B and 9C can include a haptic system 915 that holds the optic of the piggyback lens 905 in place when implanted in the eye. The haptic system 915 can comprise a biocompatible material that is suitable to engage the capsular bag of the eye, the iris 26, the sulcus and/or the ciliary muscles of the eye. For example, the haptic can comprise materials such as acrylic, silicone, polymethylmethacrylate (PMMA), block copolymers of styrene-ethylene-butylene-styrene (C-FLEX) or other styrene-base copolymers, polyvinyl alcohol (PVA), polystyrene, polyurethanes, hydrogels, etc. In various embodiments, the haptic system 915 can include a one or more arms that are coupled to the optic of the piggyback lens 905. For example, as shown in FIGS. 9B and 9C the haptic system 915 can include arms 916a and 916b that radiate outward from the periphery optic of the piggyback lens 905. The arms 916a and 916b can include a first end that is coupled to the optic of the piggyback lens 905 and a second free end that is configured to be anchored with an anatomical part of the eye (e.g., sulcus, ciliary body, etc.). In various embodiments, one or more arms of the haptic system 915 can protrude into the optic of the piggyback lens 905. In various embodiments, the peripheral portions of the one or more arms of the haptic system 915 can be curved (e.g., hooked or having a C, S or J shape) so as to securely engage the capsular bag, the zonules, the ciliary bodies, the sulcus or any other anatomy of the eye which the haptics are configured to engage. In various embodiments, the one or more arms of the haptic system 915 can be curved in the plane of the optic of the optic of the piggyback lens 905. In some embodiments, the one or more arms haptic system 915 can be curved in a plane different from the plane including the optic of the piggyback lens.

In various embodiments, the haptic system 915 can be transmissive and have a transmissivity that is substantially equal to (e.g., within about 20%) of the transmissivity of the optic of the piggyback lens 905. In various embodiments, the material of the haptic system 915 can have a refractive index that is substantially equal to (e.g., within about 20%) of the refractive index of the material of the optic of the piggyback lens 905.

Figures 2, 9E:
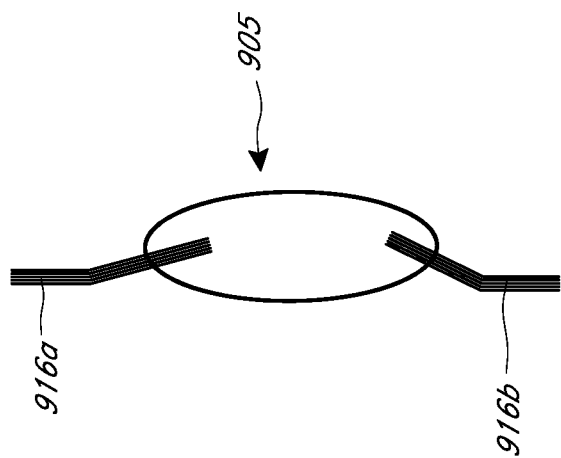
Figures 1, 9E:
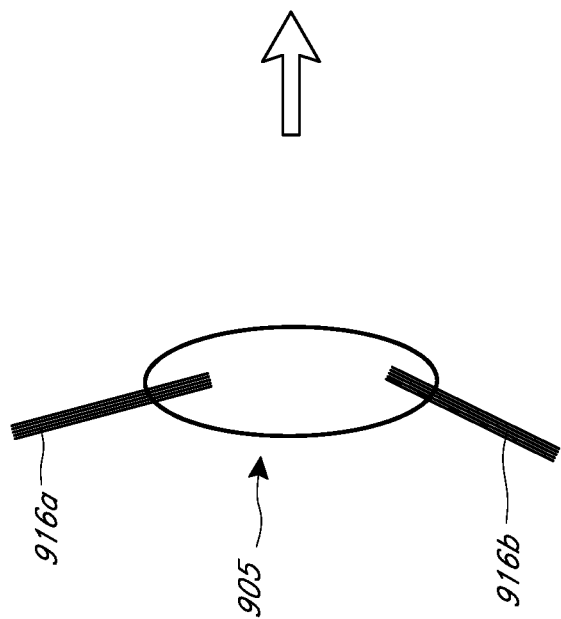

As discussed above, some embodiments of piggyback lens 905 disclosed herein can be configured to be placed in the sulcus. In such embodiments, the length of the arms 916a and 916b either alone or in combination with other parts of the haptic system 915 can be substantially equal (e.g., within about 20%) of the length of the haptic arms of a standard sulcus lens. For example, the length of the arms 916a and 916b either alone or in combination with other parts of the haptic system 915 can be around 3.5 mm. The length of the arms can be based on the intended position of the existing IOL 910, the intended displacement of the existing IOL 910 and/or the intended compression of the existing IOL 910. In various embodiments, the intended compression of the existing IOL 910 and/or the elasticity of the haptic system 915. For example, the arms 916a and 916b can be configured to be linear as illustrated in FIG. 9E-1 prior to implantation in the sulcus and can be configured to flex or bend as shown in FIG. 9E-2 when implanted in the sulcus.

The length of the arms can be between about 2-5 mm. For example, the length of the arms can be between about 2.5 mm and about 4.5 mm, between about 2.9 mm and about 4.2 mm, between about 3.0 mm and about 4.0 mm or values in any of these ranges/sub-ranges.

The haptic arms 916a and 916b can be angulated by an amount that is sufficient to displace the IOL 910 posteriorly towards the retina when the piggyback lens 905 is implanted in the eye. For example, the haptic arms 916a and 916b can be disposed at a haptic angle α with respect to an axis 930 in the plane of the optic of the piggyback lens 905 and passing through the region where the haptic arms are attached to the optic of the piggyback lens 905. Angulating the haptic arms 916a and 916b can effectively push the existing IOL 910 rearward by an amount, 'd' between about 2-4 mm.

The length of the arms 916a and 916b can depend on the diameter of the sulcus which can be between about 10.0 mm and about 14.0 mm, the separation between the haptic junctions along the diameter of the sulcus and the haptic angle α. For example, if the sulcus has a diameter of 11.0 mm, and the separation between the haptic junctions along the diameter of the sulcus (which is parallel to the axis 930) is 5.0 mm and the haptic angle is 45 degrees, the projection of the length of arms 916a and 916b along the diameter of the sulcus (which is parallel to the axis 930) is about 3.0 mm. Accordingly, the length of arms 916a and 916b given by the equation (3.0/cosine(45)) is about 4.25 mm if the haptics are rigid. The length of the arms 916a and 916b can be different if the haptics comprise an elastic material and can be compressed. For example, in some embodiments, the arms 916a and 916b can be compressed by about 2-4 mm. Accordingly, in such embodiments the length of the arms 916a and 916b can be greater than the length of arms 916a and 916b if they comprised a rigid material.

In various embodiments, the diameter of the sulcus can be measured pre operatively by diagnostic methods, such as, for example, MRI or some other diagnostic method or determined from biometric data (e.g., eye length and thickness of the crystalline lens or age of the patient) and the length of the arms 916a and 916b can be sized in accordance with the measured or determined sulcus diameter so as to displace the existing IOL 910 rearward by the desired amount.

In various embodiments of piggyback lenses disclosed herein, the haptic angle $\alpha$ can be greater than the haptic angle of standard sulcus lenses. For example, the haptic angle $\alpha$ can be greater than or equal to 15 degrees and less than or equal to about 50 degrees. For example, the haptic angle $\alpha$ can be greater than or equal to 20 degrees and less than or equal to about 45 degrees, can be greater than or equal to 25 degrees and less than or equal to about 40 degrees, can be greater than or equal to 30 degrees and less than or equal to about 35 degrees, or any value in the above described ranges/sub-ranges. In various embodiments, the haptic angle $\alpha$ can change after implantation of the IOL 905 in the sulcus. For example, the haptic angle $\alpha$ can increase after implantation of the IOL 905 in the sulcus. In some embodiments, the haptic angle $\alpha$ can increase from 0 degrees to about 45 degrees in the un-implanted configuration to about 15 degrees to about 60 degrees when implanted in the sulcus of the eye.

Consider an embodiment of a piggyback lens 905 having a haptic arm with a length of 3.5 mm attached to the optic of the piggyback lens 905 at a haptic angle of 15 degrees. After implantation, the piggyback lens 905 can displace the existing IOL 910 by an amount greater than or equal to 3.5*sin(15)=0.9 mm depending on the size of the projections 917. The amount of displacement that can be provided by the angulation of the haptic arms of the piggyback lens can depend on a variety of factors including but not limited to the haptic angle, the length of the haptic arm, the length of the projections of the piggyback lens, the resilience of the IOL 910 and/or the resistance provided by portions of the posterior cavity of the eye (e.g., parts of the capsular bag, vitreous humour, etc.).

In various embodiments, the haptic system 915 can be configured to move the optic of the piggyback lens 905 along the optical axis of the eye to displace the IOL 910 by an additional amount. For example, the haptic system 915 can include one or more hinges to facilitate axial movement of the piggyback lens. As another example, the haptic system 915 can include springs or be configured to be spring-like to effect movement of the piggyback lens 905.

In various embodiments, the portions of the haptic system 915 (e.g. haptic arms 916a and 916b) can be configured to be stiff such that the piggyback lens 905 when connected to the existing IOL 910 as discussed above can displace the existing IOL 910 by virtue of the angulated haptics of the piggyback lens 905. In various embodiments, the haptic arms 916a and 916b can be configured to be stiffer along axial direction 935.

The haptic arms 916a and 916b can be configured to be stiffer by one or more of the following approaches:

Approach I

In various embodiments, a first end of the arm 916a and 916b that is connected to the optic of the piggyback lens 905 can be expanded such that the arm 916a and 916b tapers from the first end towards the second end. In various embodiments, the first end of the arm 916a and 916b can be expanded along the axial direction 935. In some such embodiments, an axial thickness of the arm 916a and 916b can be constant from the base 918 to the periphery. FIG. 9D illustrates a front view of a piggyback lens 905 in which the arms 916a and 916b have an expanded base 918. The base 918 can have a triangular shape, a L-shape, an arcuate shape, a trapezoidal shape or some other shape that is compatible with an expanded base and a tapered peripheral portion. Embodiments of the haptics with expanded bases are described in U.S. Pat. No. 5,549,669, which is incorporated by reference herein in its entirety.

Approach II

In various embodiments, parts of the haptic system 915 (e.g., portions of the one or more haptic arms 916a and 916b) can be made stiff by forming the parts of the haptic system 915 (e.g., portions of the one or more haptic arms 916a and 916b) by a stiff material, such as, for example, cross linked material, rubber, PMMA, etc. Examples of haptics including stiff material are described in U.S. Pat. No. 6,533,814, which is incorporated by reference herein in its entirety. In various embodiments, the haptic system 915 can comprise materials such as, for example, PMMA, polyimide, PVDF and/or prolenes Approach III In various embodiments, parts of the haptic system 915 (e.g., portions of the one or more haptic arms 916a and 916b) can comprise an elastic material with reduced or no viscoelastic properties. For example, parts of the haptic system 915 (e.g., portions of the one or more haptic arms 916a and 916b) can comprise a material that shows reduced or no relaxation over time. In this manner, the parts of the haptic system 915 (e.g., portions of the one or more haptic arms 916a and 916b) can be made stiffer.

In various embodiments, parts of the haptic system 915 (e.g., portions of the one or more haptic arms 916a and 916b) can comprise materials such as, for example, Peek or polysulfon. In some embodiments, parts of the haptic system 915 (e.g., portions of the one or more haptic arms 916a and 916b) can comprise a memory materials. For example, in some embodiments, the parts of the haptic system 915 (e.g., portions of the one or more haptic arms 916a and 916b) can comprise metal like structures which change their shape when heated. The IOL 905 comprising a memory material can be configured such that the in the un-implanted configuration, the arms 916a and 916b can be stiff when extended and have a desired vaulted shape in the implanted configuration.

Modifying Anatomy of the Eye

As discussed above, the displacement of the existing IOL can depend on a variety of factors including but not limited to the resistance offered by portions of the posterior cavity (e.g. parts of the capsular bag 20, vitreous humour, etc.) of the eye. Accordingly, it may be advantageous to remove portions of the posterior cavity (e.g. parts of the capsular bag 20, vitreous humour, etc.) of the eye to reduce resistance to the displacement of the existing IOL towards the retina. Removing portions of the capsular bag can make it more flexible and reduce resistance offered by the capsular bag 20 to the posterior displacement of the IOL. Removing portions of the vitreous humour can create space posterior to the capsular bag to facilitate displacement of the IOL towards the retina. In various embodiments, the capsular bag 20 can be made more flexible by perforating the capsular bag in order to reduce resistance to the rearward displacement of the IOL. These and other related concepts are discussed herein with reference to FIGS. 10A-1-11B.

Figures 2, 10A:
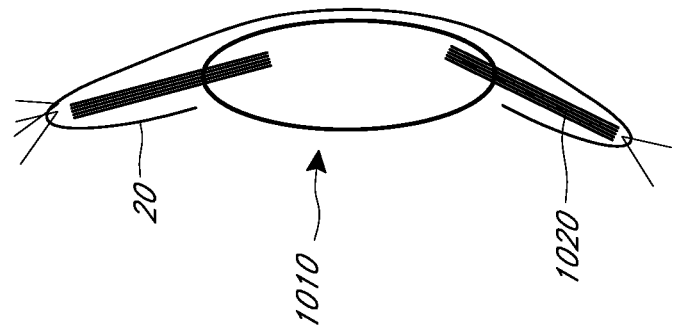
Figures 1, 10A:
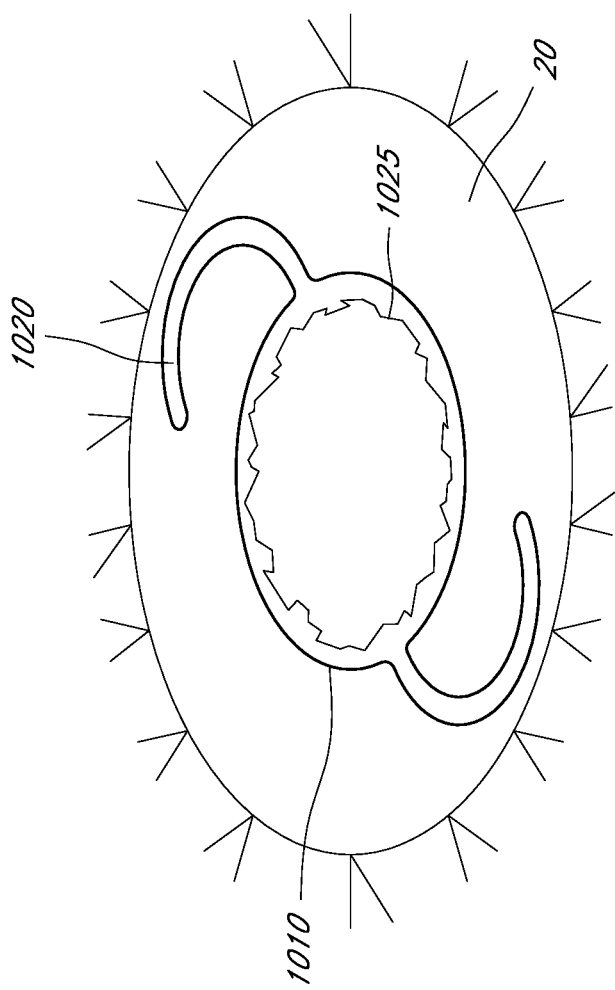

FIG. 10A-1 illustrates the top view of an IOL 1010 positioned in the capsular bag 20 of an eye. The IOL 1010 is inserted into the capsular bag 20 via a capsulorhexis formed in a capsulotomy during which a part of the anterior portion of the capsular bag 20 is removed. Generally, a capsulorhexis is formed when only a part of the anterior portion of the capsular bag 20 is removed and the posterior portion and/or the peripheral portions of the capsular bag 20 are left intact. The part of the anterior portion of the capsular bag 20 that is removed generally corresponds to the optical portion of the IOL 1010. FIG. 10A-2 depicts a side-view of the IOL 1010 inserted into a capsular bag 20 via the capsulorhexis. As shown, only a part of the anterior portion of the capsular bag 20 that overlaps with the optical portion of the IOL 1010 has been removed and other portions of the capsular bag are left intact. The portions of the capsular bag 20, such as, for example, the posterior portion of the capsular bag 20 can resist the posterior movement of the IOL 1010 such that a larger amount of force $F_{PB}$ may be required to push the IOL 1010 rearwards towards the retina.

Accordingly, portions of the anterior, posterior and/or peripheral portions of the capsular bag 20 can be removed as shown in FIGS. 10B-1 and 10B-2 to facilitate posterior movement of the IOL 1010 without requiring a large amount of force $F_{PB}$. FIG. 10B-1 illustrates the top view of an IOL 1010 positioned in a capsular bag 20 of an eye. Portions 1015 of the capsular bag are removed to reduce resistance provided by the capsular bag 20 to the positive movement of the IOL 1010. FIG. 10B-2 illustrates the side view of the IOL implanted in a capsular bag 20 portions of which have been removed. In FIG. 10B-2, the portions of the capsular bag 20 adjacent to the arms of the haptic 1020 are removed while portions of the capsular bag adjacent the posterior surface of the optical portion of the IOL 1010 are retained. It is further noted from FIG. 10B-2 that portions of the capsular bag 20 that anchor the arms of the haptic 1020 are also retained. In other embodiments, however, portions of the capsular bag adjacent to posterior surface of the optical portion of the IOL 1010 can be removed entirely or partially.

Figure 10D:
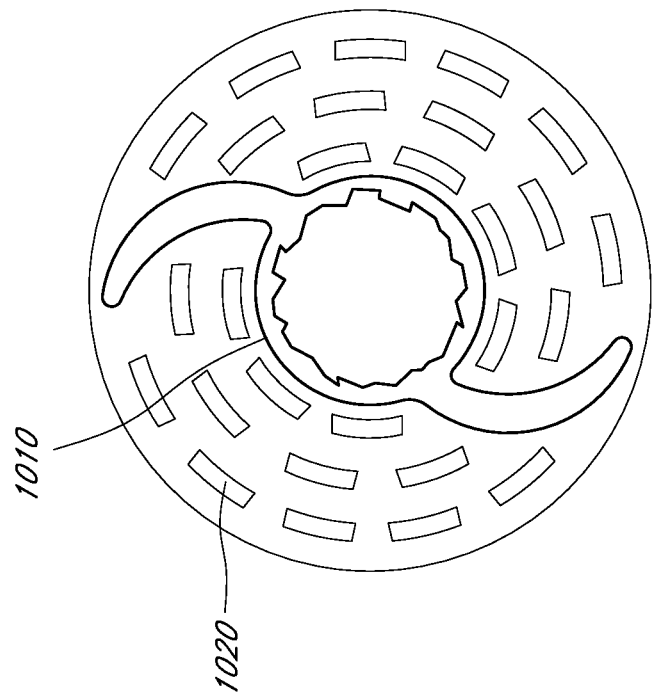
FIG. 10D illustrates the top view of an IOL positioned in a capsular bag of an eye, portions of the capsular bag include a plurality of slits to increase flexibility.
Figure 10C:
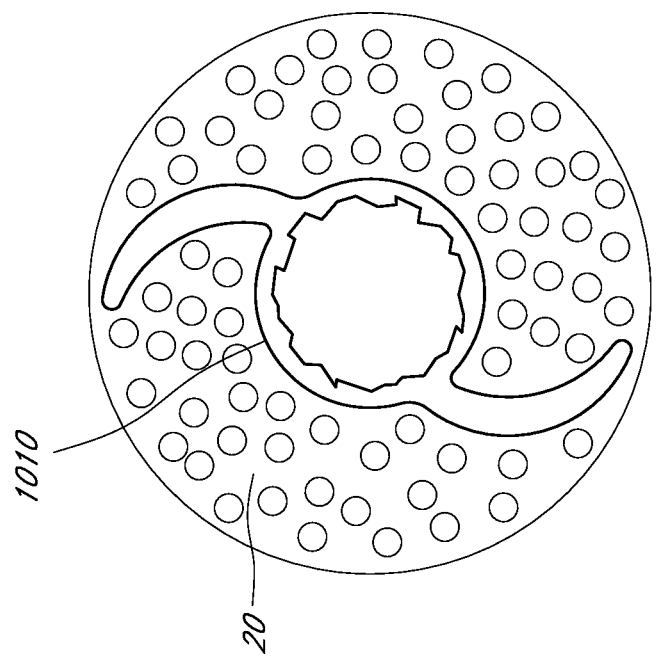
FIG. 10C illustrates the top view of an IOL positioned in a perforated capsular bag of an eye.

In some embodiments, instead of removing portions of the capsular bag adjacent to the arms of the haptic 1020 and/or the posterior surface of the optical portion of the IOL 1010, the capsular bag can perforated. For example, the capsular bag 20 can be perforated with holes as shown in FIG. 10C which illustrates the top view of an IOL 1010 positioned in a perforated capsular bag 20 of an eye. As another example, a plurality of slits or cuts can be made in to the capsular bag 20 to increase the flexibility of the capsular bag, as shown in FIG. 10D which illustrates the top view of an IOL 1010 positioned in a capsular bag 20 of an eye which includes a plurality of slits.

In some embodiments, instead of removing portions of the capsular bag adjacent to the arms of the haptic 1020 and/or the posterior surface of the optical portion of the IOL 1010, the capsular bag can perforated (e.g., include holes). FIG. 10C illustrates the top view of an IOL 1010 positioned in a perforated capsular bag 20 of an eye.

Portions of the capsular bag can be removed, perforated or slits can be created therein using systems and equipments that are used to perform capsulorhexis. For example, in various embodiments, a laser (e.g., a femtosecond laser or a Nd-YAG laser) used in cataract surgery to perform capsulorhexis can be used to remove parts of the capsular bag 20, perforate the capsular bag 20 or create slits in the capsular bag 20. For those patients in which the standard IOL and the piggyback lens that pushes the standard IOL are implanted at the same time, parts of the capsular bag 20 can be removed, perforated or slits can be created therein at the time of performing the capsulorhexis.

As discussed above, removing parts of the capsular can increase the flexibility of the lens capsule in the axial direction which can advantageously reduce resistance to the posterior displacement of the IOL. It is also noted that the connection between the piggyback lens and/or the structures that maintain centration/orientation of the IOL can be useful to maintain centration of the IOL and prevent tilt even when portions of the capsular bag 20 are removed.

Figure 11B:
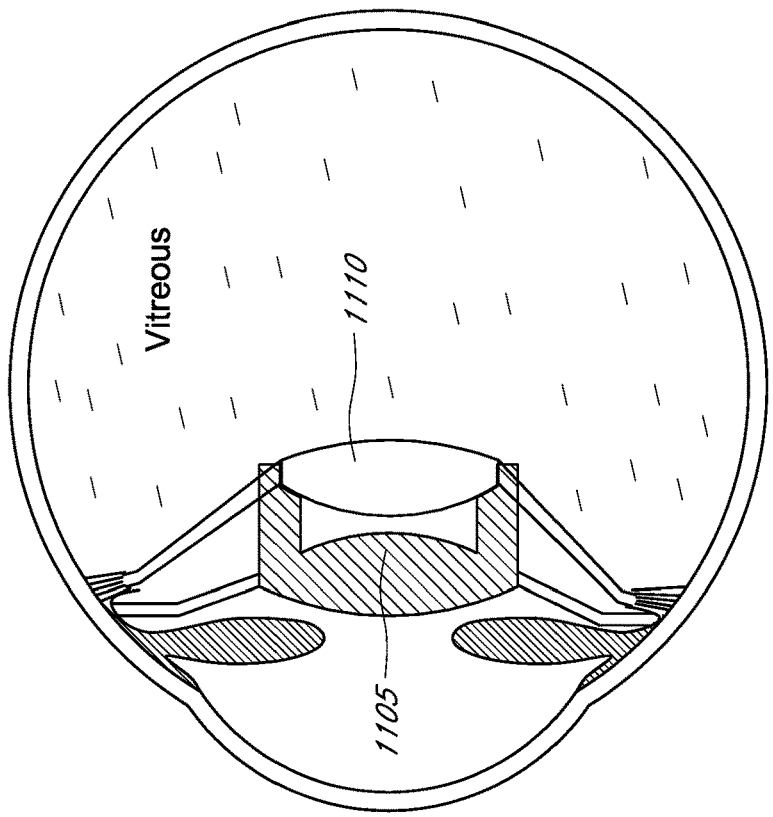
FIG. 11B illustrates a sulcus implanted piggyback lens that is used to push the existing lens into the space created in the vitreous humour.
Figure 11A:
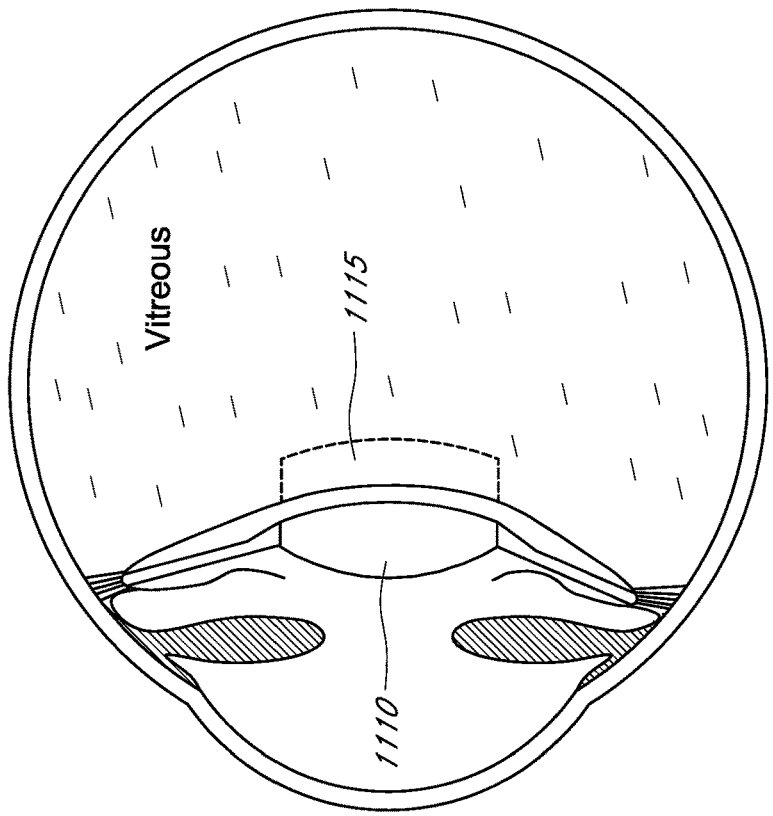
FIG. 11A illustrates an embodiment in which a hollow space that is devoid of vitreous humour is created behind the capsular bag and the existing IOL by removing or perforating part of the posterior portion of the capsular bag and remove parts of the vitreous humour through the holes in the existing portion of the capsular bag.

In various embodiments, it may be desirable to push the existing IOL farther back than the posterior extent of the capsular bag 20. In such embodiments, the vitreous humour may block the posterior displacement of the existing IOL to its desired position. Accordingly, parts of the vitreous humour can be removed to make space for the existing IOL. Portions of the vitreous humour can be removed using systems and equipments that are used to perform capsulorhexis. For example, in various embodiments, a laser (e.g., a femtosecond laser or a Nd-YAG laser) can be used to remove parts of the vitreous and create a hollow space into which the existing IOL can be pushed. FIG. 11A illustrates an embodiment in which a hollow space 1115 that is devoid of vitreous humour is created behind the capsular bag 20 (and the existing IOL 1110) by removing or perforating part of the posterior portion of the capsular bag and remove parts of the vitreous humour through the holes in the existing portion of the capsular bag. A sulcus implanted piggyback lens 1105 can be used to push the existing lens 1110 into the space 1115, as shown in FIG. 11B.

The vitreous humour has a refractive index that is close to the aqueous humour. The vitreous humour can have sufficient consistency/viscosity such that the existing IOL 1110 can fit into the created space 1115 without the vitreous humour leaking out or without affecting the optical quality of the image produced by the IOL 1110.

CONCLUSION

The above presents a description of systems and methods contemplated for carrying out the concepts disclosed herein, and of the manner and process of making and using it, in such full, clear, concise, and exact terms as to enable any person skilled in the art to which it pertains to make and use this invention. The systems and methods disclosed herein, however, are susceptible to modifications and alternate constructions from that discussed above which are within the scope of the present disclosure. Consequently, it is not the intention to limit this disclosure to the particular embodiments disclosed. On the contrary, the intention is to cover modifications and alternate constructions coming within the spirit and scope of the disclosure as generally expressed by the following claims, which particularly point out and distinctly claim the subject matter of embodiments disclosed herein.

Although embodiments have been described and pictured in an exemplary form with a certain degree of particularity, it should be understood that the present disclosure has been made by way of example, and that numerous changes in the details of construction and combination and arrangement of parts and steps may be made without departing from the spirit and scope of the disclosure as set forth in the claims hereinafter.

What is claimed is:
1. An intraocular lens system comprising:
an intraocular lens (IOL) comprising an optic and a haptic system with at least one arm attached to the optic and an annular structure that maintains centration and/or orientation of the intraocular lens, wherein the haptic system holds the optic in place when implanted in an eye, wherein the annular structure is integrated with the haptic system and is disposed at least partially about a periphery of the optic to maintain the centration and/or orientation, and a piggyback lens comprising a posterior displacer that extends posteriorly from the piggyback lens and is configured to contact the intraocular lens and push the intraocular lens rearward from its original location to a displaced location such that an axial position of the optic is displaced farther from an iris of the eye in comparison to an original axial position of the optic, wherein the posterior displacer includes one or more projections, wherein each projection includes a distal end connected to the annular structure.

2. The intraocular lens system of claim 1, wherein the annular structure is contiguous and completely surround the periphery of the optic.

3. The intraocular lens system of claim 1, wherein the annular structure includes grooves to facilitate attachment with the piggyback lens.

4. The intraocular lens system of claim 1, wherein when implanted in the eye, the posterior displacer and the haptic system hold the optic such that an anterior surface of the optic is about 0.5mm rearward of the iris of the eye.

5. The intraocular lens system of claim 1, wherein when implanted in the eye, the posterior displacer and the haptic system hold the optic such that an anterior surface of the optic is about 0.9 mm rearward of the iris of the eye.

6. The intraocular lens system of claim 1, wherein when implanted in the eye, the posterior displacer and the haptic system hold the optic such that an anterior surface of the optic is about 0.5mm to 0.9 mm rearward of the iris of the eye.

7. The intraocular lens system of claim 1, wherein the at least one arm of the haptic system is curved in a plane of the optic.

8. The intraocular lens system of claim 1, wherein the at least one arm of the haptic system is curved in a first plane that is different from a second plane including the optic.

9. The intraocular lens system of claim 1, wherein the annular structure comprises a material having rigidity or stiffness to maintain centration and/or orientation.

10. The intraocular lens system of claim 1, wherein the annular structure is discontiguous and comprises a first portion and a second portion spaced apart by a first gap and a second gap between the two portions of the annular structure.

11. The intraocular lens system of claim 10, wherein the gaps between the two portions of the annular structure overlap with a region where the at least one haptic arm is attached to the optic.

\* \* \* \* \*